US012746137B2

(12) United States Patent
Chu

(10) Patent No.: US 12,746,137 B2
(45) Date of Patent: Sep. 29, 2026

(54) DEVICES, SYSTEMS, AND METHODS FOR EXTRACTING A URETERAL STENT

(71) Applicant: BOSTON SCIENTIFIC SCIMED, INC., Maple Grove, MN (US)

(72) Inventor: Michael S H Chu, Brookline, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1067 days.

(21) Appl. No.: 17/828,146

(22) Filed: May 31, 2022

(65) Prior Publication Data

US 2022/0387056 A1 Dec. 8, 2022

Related U.S. Application Data

(60) Provisional application No. 63/196,325, filed on Jun. 3, 2021, provisional application No. 63/196,330, filed on Jun. 3, 2021.

(51) Int. Cl.

| | |
|---|---|
| ***A61F 2/95*** | (2013.01) |
| ***A61B 17/22*** | (2006.01) |
| ***A61F 2/94*** | (2013.01) |
| *A61B 17/00* | (2006.01) |
| *A61B 90/00* | (2016.01) |
| *A61M 27/00* | (2006.01) |

(52) U.S. Cl.

CPC ...... *A61F 2/9517* (2020.05); *A61B 17/22031* (2013.01); *A61F 2/94* (2013.01);

(Continued)

(58) Field of Classification Search

CPC .......... A61F 2/9517; A61F 2/95; A61F 2/966; A61F 2002/9665; A61F 2002/9505;

(Continued)

(56) References Cited

U.S. PATENT DOCUMENTS 6,569,181 B1 5/2003 Burns
2002/0161389 A1* 10/2002 Boyle .................... A61F 2/013
606/200

(Continued)

FOREIGN PATENT DOCUMENTS

CN 109172040 B 5/2021
WO WO-0203889 A2 * 1/2002 .......... A61F 2/9517

(Continued)

OTHER PUBLICATIONS

International Search Report and Written Opinion dated Sep. 26, 2022 for International Application No. PCT/US2022/031513.

*Primary Examiner* — Wesley G Harris
(74) *Attorney, Agent, or Firm* — Seager Tufte Wickhem LLP

(57) ABSTRACT

The present disclosure relates generally to devices, systems, and methods for extracting ureteral stent from a patient. Some embodiments are particularly directed to an extraction tool capable of extending into a urethra and retrieving a stent without scope visualization, assistance from a medical professional, and/or prescription medication (e.g., for pain). The extraction tool may be a single-use tool having an end effector configured to capture a proximal portion of a stent. In several embodiments, the extraction tool be utilized in conjunction with a stent assembly having a band coupled to a proximal retention member of the stent.

20 Claims, 16 Drawing Sheets

(52) U.S. Cl.
CPC ...... *A61F 2/95* (2013.01); *A61B 2017/00473* (2013.01); *A61B 2090/0807* (2016.02); *A61B 2090/0814* (2016.02); *A61F 2002/9511* (2013.01); *A61F 2002/9528* (2013.01); *A61F 2210/0014* (2013.01); *A61M 27/008* (2013.01)

(58) Field of Classification Search
CPC .............. A61F 2/962; A61F 2002/9528; A61F 2220/0016; A61B 18/1492; A61B 17/22031; A61B 2017/00473; A61B 2090/0807; A61M 27/008
See application file for complete search history.

(56) References Cited

U.S. PATENT DOCUMENTS

| | | | | |
|---|---|---|---|---|
| 2004/0186511 | A1 | 9/2004 | Stephens et al. | |
| 2006/0162731 | A1 | 7/2006 | Wondka et al. | |
| 2007/0167677 | A1 * | 7/2007 | Chu | A61B 17/29 600/104 |
| 2010/0240951 | A1 | 9/2010 | Catanese, III et al. | |
| 2010/0274187 | A1 * | 10/2010 | Argentine | A61M 25/0082 623/1.11 |
| 2011/0301685 | A1 * | 12/2011 | Kao | A61F 2/9661 623/1.11 |
| 2016/0270914 | A1 * | 9/2016 | Krans | A61F 2/2436 |
| 2018/0125511 | A1 * | 5/2018 | Chu | A61B 17/221 |
| 2019/0307563 | A1 * | 10/2019 | Sandstrom | A61F 2/2418 |

FOREIGN PATENT DOCUMENTS

| | | | | |
|---|---|---|---|---|
| WO | 2008124844 | A1 | 10/2008 | |
| WO | WO-2009013642 | A1 * | 1/2009 | A61F 2/9517 |
| WO | 2009042736 | A1 | 4/2009 | |
| WO | 2010123664 | A1 | 10/2010 | |
| WO | 2013171007 | A1 | 11/2013 | |
| WO | 2018183393 | A1 | 10/2018 | |

* cited by examiner

DEVICES, SYSTEMS, AND METHODS FOR EXTRACTING A URETERAL STENT

RELATED APPLICATIONS

This application claims the benefit of priority under 35 U.S.C. § 119 to U.S. Provisional Patent Application titled "Devices, Systems, and Methods for Ureteral Stents", No. 63/196,330, filed Jun. 3, 2021, the entire disclosure of which is hereby incorporated by reference herein for all purposes.

This application claims the benefit of priority under 35 U.S.C. § 119 to U.S. Provisional Patent Application titled "Devices, Systems, and Methods for Extracting a Ureteral Stent" No. 63/196,325, filed Jun. 3, 2021, the entire disclosure of which is hereby incorporated by reference herein for all purposes.

FIELD

The present disclosure relates generally to the field of medical devices. In particular, the present disclosure relates to devices, systems, and methods for extracting ureteral stents.

BACKGROUND

In medicine, a stent is typically a tube inserted into the lumen of an anatomic vessel or duct in order to keep the passageway open. There is a variety of stents that are utilized for different purposes. One type of stent, a ureteral stent, includes a tube inserted into the ureter to prevent or treat obstruction of urine flow from the kidney to the bladder. A stent is usually inserted by a doctor with the aid of a cystoscope. After a period of time the patient no longer needs the stent to keep the passageway open and the stent is removed. Sometimes a stent is removed using a piece of suture attached to the stent that is left hanging out of a patient. However, oftentimes the piece of suture may be removed when the stent is placed to avoid patient discomfort. In such times, a doctor may use a cystoscope in conjunction with one or more tools to retrieve the stent.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one aspect, the present disclosure relates to a medical device comprising an interface, an end effector, and a handle body. The interface may be coupled to a proximal portion of an interface shaft. A distal portion of the interface shaft may include a pin. The end effector may be coupled to a distal portion of an inner shaft. The handle body may be coupled to the distal portion of the interface shaft and a proximal portion of the inner shaft. The handle body may include a slot configured to receive the pin of the interface shaft and guide motion of the interface and the end effector with respect to the handle body.

In some embodiments, the slot is configured to interact with the pin to restrict motion of the interface and the end effector in at least one direction with respect to the handle body. In various embodiments, displacement of the interface along a longitudinal axis causes displacement of the end effector along the longitudinal axis. In several embodiments, the slot is configured to interact with the pin to cause the end effector to rotate about a longitudinal axis in response to displacement of the interface along the longitudinal axis. In many embodiments, the slot comprises a helical shape or an oval shape. In some embodiments, the slot extends about an inner circumference of the handle body at a first location to form a first circle. In some such embodiments, the slot extends about an inner circumference of the handle body at a second location to form a second circle, and the slot connects the first and second circles. In various embodiments, the inner shaft is flexible. In several embodiments, the inner shaft is pre-curved. Many embodiments include an outer shaft with a proximal end coupled to the handle body and a distal end coupled to an effector shield, and the inner shaft may be disposed within the outer shaft. In many such embodiments, the effector shield has an outer diameter greater than an outer diameter of the end effector. In some embodiments, the end effector comprises a plurality of spiral slots or a hook. In various embodiments, the handle body includes an indicator window and the interface shaft including a first indicator and a second indicator, wherein the first indicator is visible via the indicator window when the end effector is in a first position relative to the handle body and the second indicator is visible via the indicator window when the end effector is in a second position relative to the handle body. In several embodiments, the inner shaft is coupled to the handle body via a biasing member. In many embodiments, the end effector, the inner shaft, and the interface shaft define a lumen configured for passage of a guidewire.

In another aspect, the present disclosure relates to a method. The method may include inserting a proximal end of an extractor into a urethra of a body. The extractor may include an interface coupled to a proximal portion of an interface shaft, an end effector coupled to a distal portion of an inner shaft, and a handle body coupled to the distal portion of the interface shaft and a proximal portion of the inner shaft. The method may include transitioning the extractor from a retracted state to an extended state to capture a stent. The method may include removing the proximal end of the extractor from the urethra to remove the stent from the body.

In various embodiments, the method includes depressing the interface to transition the extractor from the retracted state to the extended state. In some embodiments, a distal portion of the interface shaft comprises a pin, and wherein the handle body includes a slot configured to receive the pin of the interface shaft and guide motion of the interface and the end effector with respect to the handle body when the extractor is transitioned from the retracted state to the extended state. In some such embodiments, the slot comprises a helical shape or an oval shape to at least partially rotate the end effector when the extractor is transitioned from the retracted state to the extended state.

In yet another aspect, the present disclosure relates to a system comprising an extractor and a stent. The extractor may include an interface, an end effector, and a handle body. The interface may be coupled to a proximal portion of an interface shaft, wherein a distal portion of the interface shaft comprises a pin. The end effector may be coupled to a distal portion of an inner shaft. The handle body may be coupled to the distal portion of the interface shaft and a proximal portion of the inner shaft, wherein the handle body includes a slot configured to receive the pin of the interface shaft and guide motion of the interface and the end effector with respect to the handle body. The stent may include a loop configured for capture by the end effector of the extractor.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. In will be appreciated that various figures included in this disclosure may omit some components, illustrate portions of some components, and/or present some components as transparent to facilitate illustration and description of components that may otherwise appear hidden. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
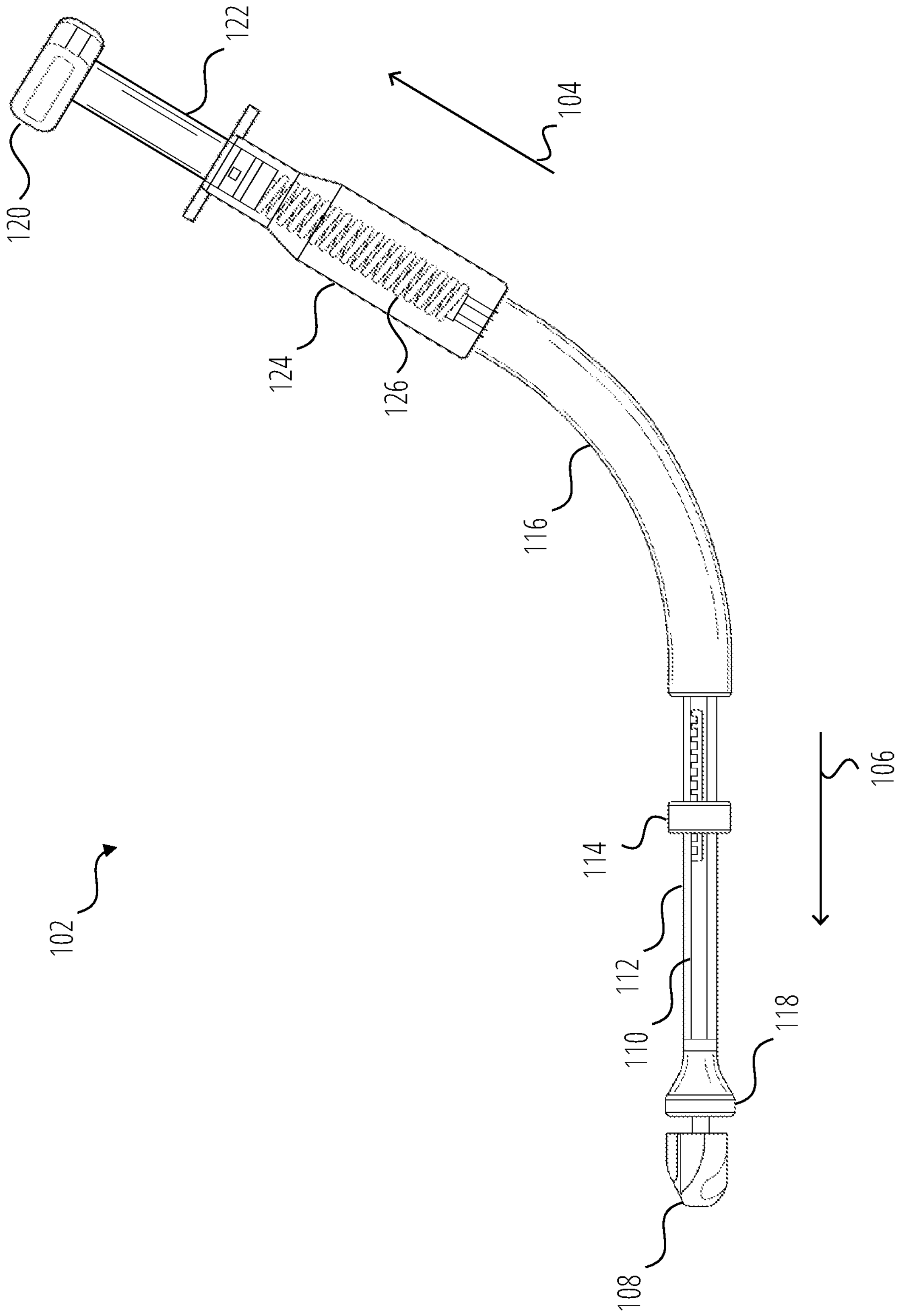
FIG. 1 illustrates an exemplary extractor according to one or more embodiments disclosed hereby.

The present disclosure relates generally to devices, systems, and methods for extracting ureteral stent from a patient. Some embodiments are particularly directed to an extraction tool capable of extending into a urethra and retrieving a stent without scope visualization, assistance from a medical professional, and/or prescription medication (e.g., for pain). However, the present disclosure is not limited to the embodiments described. The terminology used herein is only for the purpose of describing particular embodiments and is not intended to be limiting. Unless otherwise defined, all technical terms used herein have the same meaning as commonly understood by one of ordinary skill in the art to which the disclosure belongs.

Although embodiments of the present disclosure may be described with specific reference to ureteral stents, it should be appreciated that such devices, systems, and methods may be used with a variety of instruments and for a variety of other tissues, body passageways, organs and/or cavities, such as the vascular system, urogenital system, upper gastrointestinal system, lower gastrointestinal system, and the like.

As used herein, a "proximal" end refers to the end of a device that lies closest to the medical professional along the device when introducing the device into a patient, and a "distal" end refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", et cetera, indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

As used herein, the conjunction "and" includes each of the structures, components, portions, or the like, which are so conjoined, unless the context clearly indicates otherwise, and the conjunction "or" includes one or the others of the structures, components, portions, or the like, which are so conjoined, singly and in any combination and number, unless the context clearly indicates otherwise.

The detailed description should be read with reference to the drawings, which are not necessarily to scale, depict illustrative embodiments, and are not intended to limit the scope of the invention.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates an exemplary extractor 102 according to one or more embodiments disclosed hereby. Extractor 102 has a proximal end 104, a distal end 106, and includes an end effector 108, an effector shield 118, an inner shaft 110, an outer shaft 112, an adjustable stop 114, curved shaft 116, handle body 124, biasing member 126, interface shaft 122, and interface 120. In various embodiments, extractor 102 may be utilized to remove a ureteral stent from a patient without the need for imaging, a medical professional, or prescription medication (e.g., for pain). In some embodiments, FIG. 1 may include one or more components that are the same or similar to one or more other components of the present disclosure. Further, one or more components of FIG. 1, or aspects thereof, may be incorporated into other embodiments of the present disclosure, or excluded from the disclosed embodiments, without departing from the scope of this disclosure. Further, one or more components of other embodiments of the present disclosure, or aspects thereof, may be incorporated into one or more components of FIG. 1, without departing from the scope of this disclosure. Embodiments are not limited in this context.

In several embodiments, extractor 102 may be utilized by a patient, patient family member, or similar to remove a ureteral stent from the patient at home without the need for imaging or assistance of a medical professional. As will be described in more detail below, such as with respect to FIGS. 2A and 2B, in many embodiments, the distal end 106 of the extractor 102 may be inserted into a urethra, such as up to the adjustable stop 114. In several embodiments, the adjustable stop 114 may prevent the end effector 108 from extending past the bulbar urethra. For example, adjustable stop 114 may have a diameter that prevents the adjustable stop 114 from entering the urethra as the proximal end 106 of extractor 102 is advanced into urethra. Accordingly, adjustable stop 114 and end effector 108 are not illustrated to scale in FIG. 1 (or the adjustable stop and end effector in FIGS. 3A and 3B). Once inside the urethra, the end effector 108 may extend distally and move in one or more other directions (e.g., rotation, lateral extension, et cetera) to capture a proximal portion of the stent (or stent assembly) in response to depressing the interface 120 and/or rotating the extractor 102. The extractor 102 may then be removed to extract the stent. The movement of the end effector due to depression of the interface 120 will be described in more detail below, such as with respect to FIGS. 5-12. The end effector 108 may come in a variety of shapes, forms, and fashions and include features to capture (e.g., entangle) a proximal portion of a stent assembly, which will be described in more detail below, such as with respect to FIGS. 13A-27B.

In some embodiments, one or more portions of the extractor 102 may be constructed from polymer. For example, each component except biasing member 126 may be constructed from one or more polymers. In various embodiments, biasing member 126 may be constructed from metal, such as stainless steel. In various embodiments, the end effector 108 may be less than 30 French in diameter, such as 8, 10, 12, 16, 18, 22, or 24 French. The end effector 108 may be atraumatic with no sharp edges or corners. In some embodiments, one or more components of extractor 102 may include ergonomic features. For example, curved shaft 116 may provide ergonomic features, such as by improving operability when the extractor 102 is used by an individual on themselves to remove a stent.

A proximal end of the inner shaft 110 may be coupled to the interface 120, such as via interface shaft 122. A distal end of the inner shaft 110 may be coupled to the end effector 108. In some embodiments, the end effector 108 and inner shaft 110 may be integrally formed (see e.g., FIGS. 17-27B). The inner shaft 110 may be disposed within outer shaft 112 (e.g., a sheath). In several embodiments, the inner shaft 110 may be flexible while the outer shaft 112 is more rigid. Accordingly, the outer shaft 112 may provide stiffness for insertion. The biasing member 126 may be coupled to the handle body 124 and one or more of the inner shaft 110 and the interface shaft 122. In various embodiments, the inner shaft 110 may be coupled to the handle body 124 via the biasing member 126. In some embodiments, biasing member 126 may maintain extractor 102 in a retracted state in the absence of external input on interface 318. In many embodiments, end effector 108 may be maneuvered to capture a stent by displacing and/or rotating interface 318.

A proximal end of the outer shaft 112 may be coupled to the handle body 124. In some embodiments, the proximal end of outer shaft 112 may be coupled to handle body 124 via curved shaft 116. In some embodiments, outer shaft 112 may extend into the curved shaft 116. In some such embodiments, a curved portion of outer shaft 112 may be used to stiffen the curved shaft 116. A distal end of the outer shaft 112 may be coupled to the effector shield 118. In various embodiments, the effector shield 118 may shield the end effector 108 during proximal movement of the extractor 102. The effector shield 118 may provide a surface to facilitate atraumatic and comfortable proximal movement of extractor 102. In several embodiments, effector shield 118 may include a diameter that is equal to or greater than the diameter of the end effector 108. In some embodiments, the end effector 108 may be molded.

In some embodiments, the distal surface of the curved shaft 116 may be used as a fixed stop for adjustable stop 114. In many embodiment, extractors may be offered in a variety of lengths and configurations for various anatomies (e.g., male or female) and/or operator preferences. In various embodiments, the extractor 102 may be configured by a medical professional, such as following insertion of the stent. For example, the medical professional that inserts a stent into a patient may select the appropriately configured extractor to send home with the patient for subsequent removal of the stent. Some configurations of extractors may be utilized in males, females, or both. In many embodiments, the extractor 102 includes one or more passages to facilitate use of a guidewire. In various embodiments, one or more portions of extractor 102 may be coated, such as with a polymer and/or a hydrophilic coating.

Figure 2A:
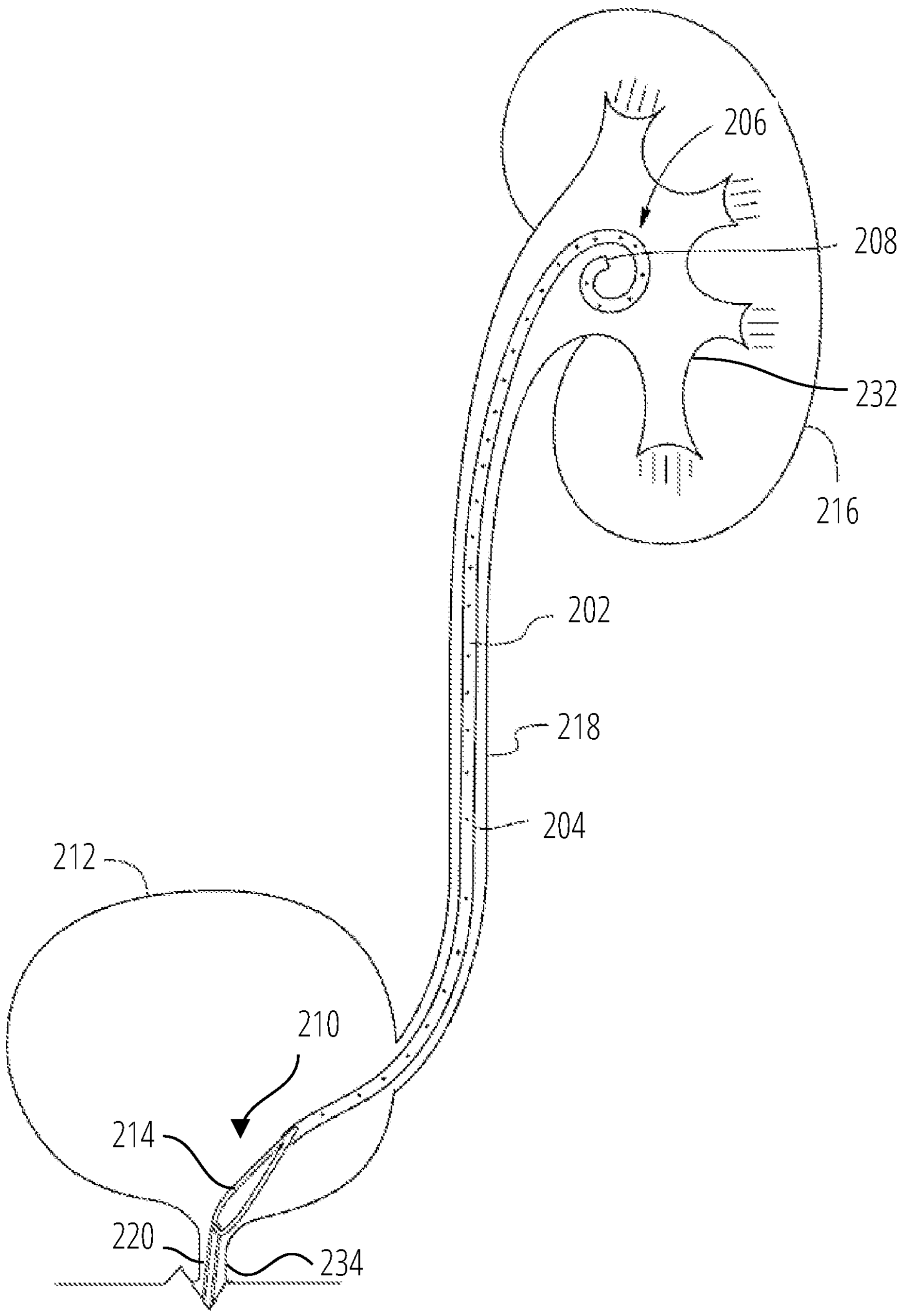
FIG. 2A illustrates various aspects of a stent positioned within a patient according to one or more embodiments disclosed hereby.
Figure 2B:
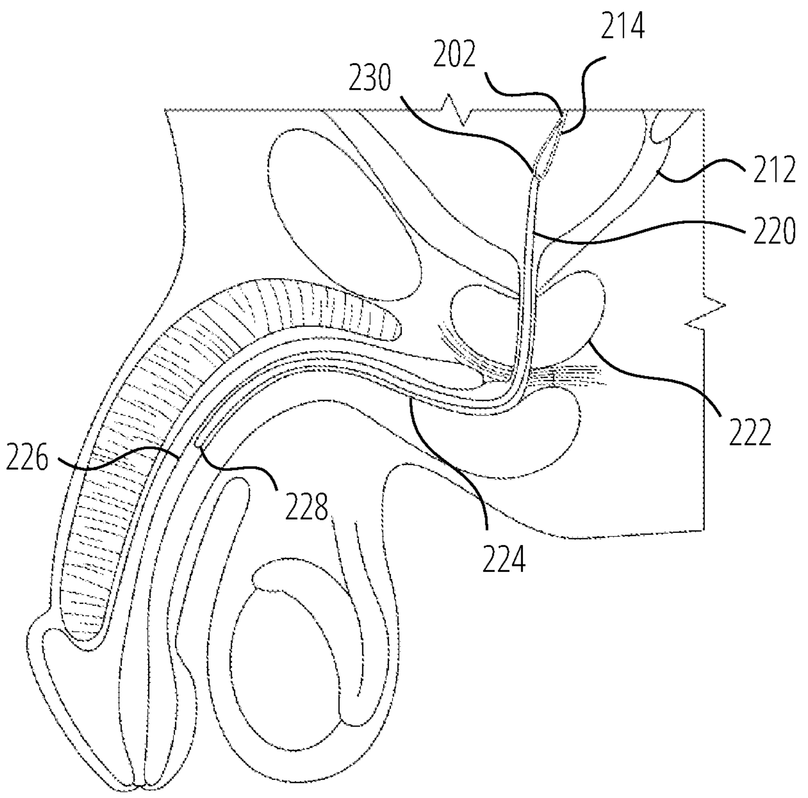
FIG. 2B illustrates various aspects of a band positioned within a patient according to one or more embodiments disclosed hereby.

FIGS. 2A and 2B illustrate various aspects of a stent assembly positioned within a patient according to one or more embodiments disclosed hereby. More specifically, FIG. 2A illustrates various aspects of a stent 202 positioned within the patient and FIG. 2B illustrates various aspects of a band 220 positioned within the patient. One or more embodiments disclosed hereby may include a medical device (e.g., extractor 102) that enables safe and efficient removal of the stent 202. In some embodiments, FIGS. 2A and 2B may include one or more components that are the same or similar to one or more other components of the present disclosure. Further, one or more components of FIGS. 2A and 2B, or aspects thereof, may be incorporated into other embodiments of the present disclosure, or excluded from the disclosed embodiments, without departing from the scope of this disclosure. Further, one or more components of other embodiments of the present disclosure, or aspects thereof, may be incorporated into one or more components of FIGS. 2A and 2B, without departing from the scope of this disclosure. For example, extractor 102 may be utilized to remove stent 202 without departing from the scope of this disclosure. In such examples, the end effector 108 may be extended into the penile urethra 226 to capture the band 220 and pull the stent 202 out. Embodiments are not limited in this context.

Referring to FIG. 2A, the stent 202 includes a proximal end 210 with a proximal retention member 214, a distal end 208 with a distal retention member 206 midportion 204, and a midportion 204 connecting the proximal and distal retention members 214, 206. Additionally, a band 220 is coupled to the proximal retention member 214 and extends into the urethra 234. In the illustrated embodiment of FIG. 2A, the proximal retention member 214 is disposed in the bladder 212, the distal retention member 206 is disposed in the renal pelvis 232 of the kidney 216, and the midportion 204 extends through the ureter 218. In various embodiments, the renal pelvis 232 may comprise an area proximate the center of the kidney 216 at which urine collects and is funneled into the ureter 218. In some embodiments, proximal retention member 214 and band 220 may be replaced with a proximal retention member comprising an extended loop. Collectively, the stent 202 and the band 220 may be referred to as a stent assembly. More generally, a stent assembly may refer to the stent and any other component coupled to the stent (e.g., a suture loop, a band, et cetera). However, as will be appreciated, sometimes the term stent may be used in place of stent assembly to refer to the stent in conjunction with one or more other components such as a band and/or suture loop.

In various embodiments, the proximal and distal retention members 112, 110 may take a variety of forms, such as a shape of a pigtail, a J-shaped curve, a loop, a cope loop, a spiral shape, a helical shape, a corkscrew shape, or a combination thereof. In the illustrated embodiment, distal retention member 110 comprises a pigtail. The proximal retention member 112 may comprise one or more loops. The one or more loops may be made of a cord material. In various embodiments, the two ends of the cord material may be integrated into the midportion 104 such that the cord ends cannot poke into tissue and cause irritation or pain. The illustrated embodiment of proximal retention member 112 includes a single loop. However, other embodiments may include more than one loop, such as two or three.

More generally, stents may be delivered into patients for various purposes including stenting, drainage, etc., of lumens, tracts, vessels, and cavities within the body. As an example, ureteral stents may be used to facilitate drainage in the upper urinary tract (e.g., drainage from the kidney to the bladder), possibly following ureteroscopy, endoureterotomy, and endopyelotomy, as well as in other instances where ureteral obstruction may occur or access to the kidney and/or ureter is otherwise warranted.

An exemplary stent of this type is illustrated in conjunction with patient anatomy in FIG. 2A. The stent 202 has a proximal end 210 and a distal end 208. It may comprise a tubular polymer extrusion having a midportion 204 (or shaft), a distal retention member 206 (e.g., a renal "pigtail"), and a proximal retention member 214 (e.g., a bladder loop). These retention members 206, 214 prevent upward migration of the stent 202 toward the kidney 216 or downward migration of the stent 202 toward the bladder 212. Once properly deployed in the ureter 218, the stent 202 supports the ureter 218 and allows the passage of urine through the stent 202 and, because the ureter 218 naturally dilates around foreign bodies, allows urine to flow around the stent 202 as well.

In various embodiments of a stent described hereby and otherwise within the scope of the present disclosure, a stent may be placed over a guidewire, through a cystoscope, a flexible ureteroscope, or the like, and advanced into a position with a delivery device that may engage and may release the stent. Once the distal end of the stent is advanced into the kidney/renal calyx, the guidewire and/or delivery device are removed, allowing retention members, such as pigtails to form in the kidney and/or bladder. The distal retention member of a stent may be closed or tapered on the end, which may depend on the method of insertion (e.g., the use of a guidewire or otherwise).

A delivered stent may cause patient discomfort or pain, for example, regarding ureteral stents, pain and/or discomfort in the bladder and flank area after insertion. For example, many stents have an extraction suture loop attached to the proximal end of the stent. Typically, the suture loop is a length of suture with the ends tied or crimped together. The suture loop may be extended external to the patient such that the stent can be removed by the body by pulling the suture loop. However, having a portion of the stent assembly extending outside of the body can lead to leakage. Also, inadvertent, or undesired pulling of the suture loop can cause pain to the patient, and can lead to dislodgement of the stent, which can cause urine to cease flowing through the ureter 218. However, leaving the suture loop inside the body can cause pain and irritation to the urinary tract, such as due to the tied or crimped ends of the suture loop irritating the urethra. For these and other reasons, some medical professionals prefer to not use the suture loop. Accordingly, they may remove the suture loop after placement of the stent, such as by cutting it off.

Further complexities are associated with removing the suture loop after placement of the stent. For example, ureteral stents are typically placed after urological procedures, such as a flexible ureteroscopy, to provide or maintain urine drainage from the kidney to the bladder. After a period of time (e.g., less than a year), the stent has served its purpose and needs to be removed from the patient. Typically, without an external suture loop end, the patient has an appointment with a medical professional to remove the stent. The medical professional may utilize a cystoscope, a retrieval device, and pain medication for the patient to remove the stent. Removal of the stent by a medical profession is time consuming and resource demanding. For example, removal of the stent can be time consuming for a doctor and require considerable resources for the medical equipment, room, labor, and stocking/reprocessing of the cystoscope.

Accordingly, many embodiments may include a medical device (e.g., extractor 102) that facilitates removal of the catheter without the help of a medical professional or requiring a portion of the stent assembly (e.g., suture loop) to extend outside of the patient. For example, the extraction may be performed without visualization using a single-use extraction tool (e.g., extractor 102). In several embodiments, the extraction tool be utilized in conjunction with a stent assembly having a band (e.g., band 220) coupled to a proximal retention member (e.g., proximal retention member 214) of the stent. In various embodiments, the band may include one or more features that promote patient comfort while the stent is positioned within a body, such as by being atraumatic and/or seamless. In other embodiments, the extraction tool may be utilized to remove stent assemblies that do not include a band, such as stent assemblies with a suture loop connected to the proximal retention member or stent assemblies with a proximal retention member that extends into the urethra (e.g., an extended proximal retention member). Various stents and stent assemblies that may be used in conjunction with the extraction tools disclosed hereby are described in U.S. Provisional Patent Application No. 63/196,325, filed Jun. 3, 2021, titled “Devices, Systems, and Methods for Ureteral Stents”, the entirety of which is incorporated herein by reference.

Referring to FIG. 2B, various aspects of the band 220 positioned with a patient is illustrated. The band 220 may include a proximal end 228 and a distal end 230 coupled to the proximal retention member 214 of stent 202. The distal end 230 of band 220 may be positioned in the bladder 212. The band 220 may extend proximally past the prostate 222 and the bulbar urethra 224, finally ending with the proximal end 228 in the penile urethra 226. In some embodiments, the proximal end 228 of band 220 may be positioned proximate the proximal end of the urethra (i.e., near the exit). For example, the distal end 230 of band 220 may be positioned as close as possible to the exterior opening of the urethra without extending outside of the patient. In various embodiments, positioning the distal end 230 of the band near the proximal end of the urethra may facilitate removal with the extraction tool. In embodiments in which an extended proximal retention member (e.g., a loop) is utilized in place of the band 220, the proximal end of the proximal retention member may be positioned in the same manner as the band 220.

In several embodiments, positioning a proximal end of the stent assembly outside of the body can lead to leakage, however, by leaving the proximal end of the stent assembly within the body, leakage may be avoided.

In various embodiments, any excess length of the band 220, or an extended proximal retention member, may be positioned within the bladder 212. For instance, the entire band 220, or extended proximal retention member, may be initially positioned within the bladder 212. Then the proximal end may be pulled into the urethra to the proper position, leaving the remainder of the band 220, or extended proximal retention member, in the bladder 212. The ability to leave excess material in the bladder 212 may enable a more adaptable stent 202 with an adjustable effective length, reducing the need for different size stents and stent assemblies. In many embodiments, the band 220, or extended proximal retention member, may be formed from a thin material that will not be pulled back into the bladder by returning to an original shape.

More generally, the urethra, which includes the bulbar urethra 224 and the penile urethra 226, may be a tubular structure that provides a passageway between the bladder 212 and the exterior of the body. Accordingly, the urethra enables urine to be excreted from the body. In several embodiments described hereby, placing a portion of the stent assembly (e.g., band 220) in the urethra may simplify locating the stent assembly for removal by an extraction devices (e.g., extractor 102). For example, when the proximal end 228 of the band 220 is confined to the tubular passage of the urethra near the outside of the body makes it more accessible than if it was positioned within the bladder. In various embodiments, a suture loop may be utilized to pull band 220 into the urethra, past the prostate 222, and past the bulbar urethra 224 to position the proximal end 228 in the penile urethra 226. In several embodiments, the proximal end 228 of the band 220 may be positioned proximal the bulbar urethra 224 to avoid patient pain or discomfort, such as during removal, because the bulbar urethra 224 is more sensitive than the penile urethra 226 in many patients.

In various embodiments, the band 220 may be coupled (e.g., looped through) to the proximal retention member 214. In some embodiments, the band 220 may be attached to the proximal retention member 214 during manufacture of the stent assembly 102. For example, the band 220 may be looped into the proximal retention member 214 when the proximal retention member 214 is attached to the midportion 204. In some embodiments, the band 114 may have a predetermined durometer and/or shape that can be different than the rest of the stent assembly 102. In many embodiments, the band 114 may be available in different lengths. For example, the male urethra may be approximately 20 cm and the female urethra may be approximately 4 cm. Accordingly, a longer band may be used for males than females.

In several embodiments, an extraction tool (e.g., extractor 102) may be utilized by a patient, patient family member, or similar to remove stent 202 from the patient at home without the need for imaging or assistance of a medical professional. In many embodiments, the distal end 106 of the extractor 102 may be inserted into the proximal end of the urethra at the penile urethra 226. In several embodiments, features of the extractor (e.g., adjustable stop 114) may prevent a distal end of the extractor from extending past the bulbar urethra 224. Once inside the urethra, the end effector of the extractor (e.g., end effector 108) may extend distally and/or move in one or more other directions (e.g., rotation, lateral extension, et cetera) to capture a proximal portion of the band 220 in response to depressing the interface (e.g., interface 120)

and/or rotating the extractor. The extractor may then be removed to extract the stent 202. In several embodiments, one or more of the end effector and the inner shaft are flexible and/or pre-curved.

Different extractors may be utilized for male and female patients. The male urethra is typically around 20 cm in length. When advancing an extractor in a male patient, advancing the extractor beyond the bulbar urethra 224 may result in undesirable pain and/or injury. Accordingly, various extractors may include a stop to prevent the extractor from extending beyond the bulbar urethra 224. In some embodiments, the stop is adjustable (see e.g., adjustable stop 314). In some embodiments, extractors configured for females may not include a stop.

On the other hand, the female urethra is typically around 4 cm in length and fused with the anterior wall of the vagina. The female urethra may terminate between the clitoris and the vagina. Since the female urethra is relatively short, it can be more common for the urethral portion of the stent to migrate into the bladder. Accordingly, in some embodiments, an extractor may be configured to advance beyond the urethra and into the bladder to capture the stent for retrieval. However, the bladder has a larger volume, leading to a more challenge capture, especially in the absence of imaging and/or a medical professional. Therefore, in many embodiments, extractors may include curved inner and/or outer shafts. In several embodiments, extractors may cause the end effector to perform a sweeping action to capture the stent. In various embodiments an extractor may be able to perform sweeps of varying angles and/or circumference. For example, small circumference sweeps may be utilized in the urethra and large circumference sweeps may be utilized in the bladder. In one embodiment, the circumference of a sweep may be controlled by the amount an inner shaft is extended out of an outer shaft (see e.g., FIG. 3B).

Figure 3A:
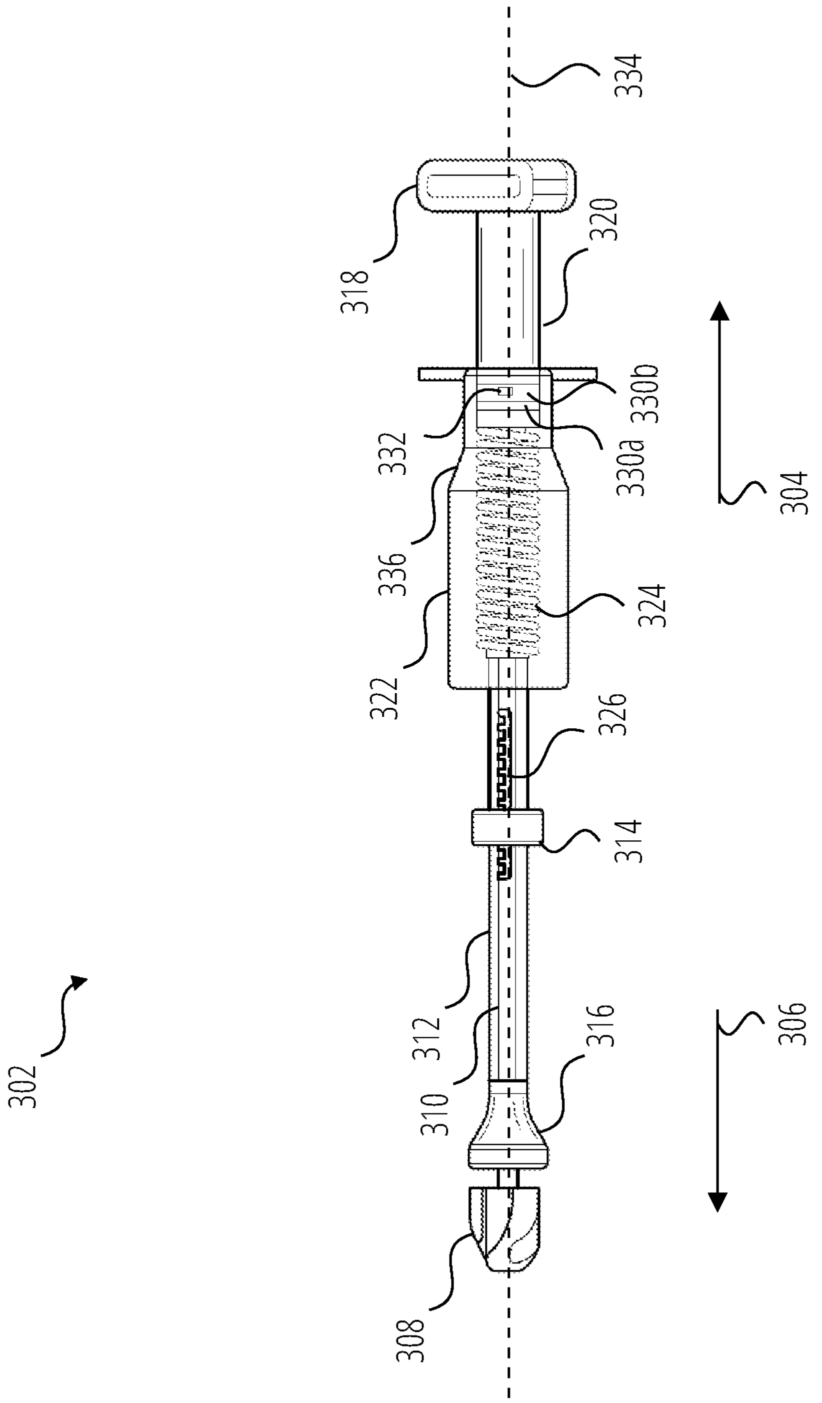
FIG. 3A illustrates an extractor in a first configuration according to one or more embodiments disclosed hereby.

FIG. 3A illustrates an extractor 302 in a first state according to one or more embodiments disclosed hereby. The extractor 302 has a proximal end 104, a distal end 306, a longitudinal axis 334, and includes end effector 308, effector shield 316, inner shaft 310, outer shaft 312, adjustable stop 314, stop track 326, handle body 322, biasing member 324, indicator 330*a*, indicator 330*b*, indicator window 332, grip feature 336, interface shaft 320, and interface 318. In the illustrated embodiments, extractor 302 is shown in a first state. The first configuration may represent a state of the extractor 302 in the absence of external input. Accordingly, the first state may correspond to a storage or retracted state of the extractor 302. In many embodiments, the extractor 302 may be in the first state when it is initially inserted into a urethra. In some embodiments, FIG. 3A may include one or more components that are the same or similar to one or more other components of the present disclosure. For example, extractor 302 may be the same or similar to extractor 102 except for the curved shaft 116. Further, one or more components of FIG. 3A, or aspects thereof, may be incorporated into other embodiments of the present disclosure, or excluded from the disclosed embodiments, without departing from the scope of this disclosure. For example, extractor 302 may be utilized to capture band 220 and remove the stent 202 of FIGS. 2A and 2B without departing from the scope of this disclosure. Further, one or more components of other embodiments of the present disclosure, or aspects thereof, may be incorporated into one or more components of FIG. 3A, without departing from the scope of this disclosure. For example, end effector 1602 of FIG. 16 may be incorporated into extractor 302 (e.g., by replacing end effector 308) without departing from the scope of this disclosure. Embodiments are not limited in this context.

In various embodiments, one of indicators 330*a*, 330*b* may be visible via indicator window 332 depending on the extension of end effector 308. In many embodiments, the indicator visible via indicator window 332 may identify whether or not a stent has been captured. For example, a stent capture may be identified due to the physical separation between end effector 308 and effector shield 316 caused by having a portion of a stent assembly captured therebetween. In some embodiments the indicators 330*a*, 330*b* may comprise colored stripes. For example, a green stripe may indicate a stent has been captured while a red stripe may indicate a stent has not been captured (due to nothing keeping end effector 308 and effector shield 316 separated. In many embodiments, adjustable stop 314 and stop track 326 may have corresponding threads. Accordingly, adjustable stop 314 may be rotated to adjust an extension length of the extractor 302. In some embodiments, grip feature 336 may provide an ergonomic surface for handling the extractor 302. In various embodiments, the handle body 322 may include features to facilitate distal movement of interface 318. For example, as shown in the illustrated embodiment, extractor 302 may include wings or ears at the proximal end of handle body 322.

Figure 3B:
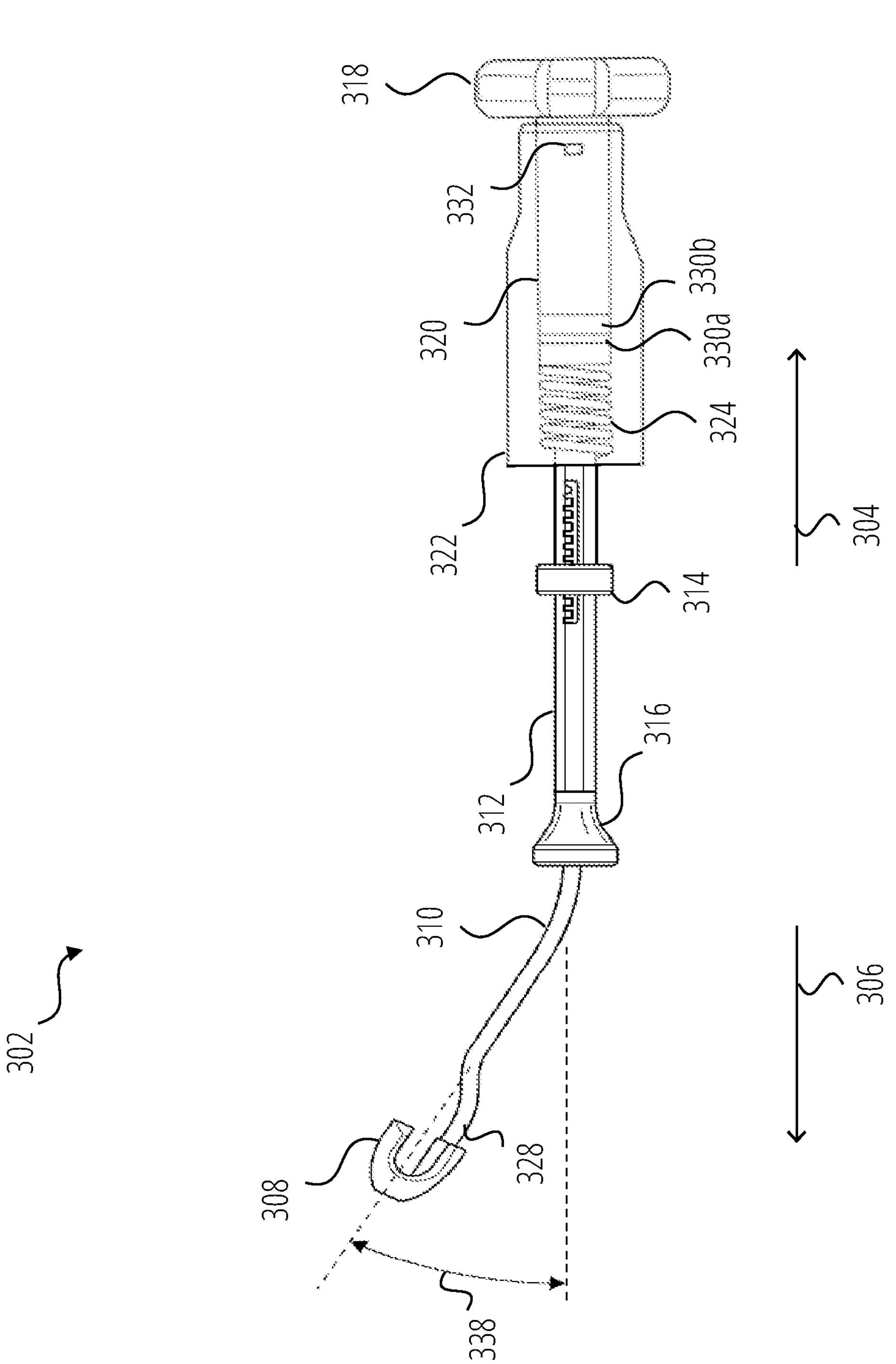
FIG. 3B illustrates an extractor in a second configuration according to one or more embodiments disclosed hereby.

FIG. 3B illustrates the extractor 302 in a second state according to one or more embodiments disclosed hereby. In addition to the components of extractor 302 identified in FIG. 3A, FIG. 3B includes shaft offset 328 and sweep angle 338. Further, FIG. 3B illustrates curvature in the inner shaft 310 that occurs when a portion of the inner shaft 310 is extended out from within the outer shaft 312, such as due to depressing interface 318. In the illustrated embodiments, extractor 302 is shown in the second state. The second state may represent a state of the extractor 302 when interface 318 is depressed. Accordingly, the second state may correspond to an acquisition or extended state of the extractor 302. In many embodiments, the extractor 302 may be transitioned from the first state to the second state to capture a proximal portion of a stent assembly within a urethra. As will be discussed in more detail below, transitioning from the first state to the second state may cause a variety of movements (e.g., lateral, longitudinal, and/or rotational) in the end effector 308 to capture the proximal portion of the stent assembly. In some embodiments, FIG. 3B may include one or more components that are the same or similar to one or more other components of the present disclosure. For example, extractor 302 may be the same or similar to extractor 102 except for the curved shaft 116. Further, one or more components of FIG. 3B, or aspects thereof, may be incorporated into other embodiments of the present disclosure, or excluded from the disclosed embodiments, without departing from the scope of this disclosure. For example, extractor 302 may be utilized to capture band 220 and remove the stent 202 of FIGS. 2A and 2B without departing from the scope of this disclosure. Further, one or more components of other embodiments of the present disclosure, or aspects thereof, may be incorporated into one or more components of FIG. 3B, without departing from the scope of this disclosure. For example, effector component 2702 of FIGS. 27A and 27B may be incorporated into extractor 302 (e.g., by replacing end effector 308 and one or more portions of inner shaft 310) without departing from the scope of this disclosure. Embodiments are not limited in this context.

In various embodiments, inner shaft 310 may have a pre-curved shape. In several embodiments, extractors may cause the end effector 308 to perform a sweeping action to capture a stent. In various embodiments an extractor may be able to perform sweeps of varying angles and/or circumference. For example, small circumference sweeps may be utilized in the urethra and large circumference sweeps may be utilized in the bladder. In such examples, handle body 322 may be the same or similar to handle body 702 of FIG. 7. In one embodiment, the circumference of a sweep may be controlled by the amount an inner shaft is extended out of an outer shaft. In many embodiments, the inner shaft 310 may be curved such that the sweep angle 338 can be controlled. For example, a large sweep angle 338 may be utilized by extending the interface 318 distally and rotating the interface 318. In such examples, handle body 322 may be the same or similar to handle body 702 of FIG. 7. As will be discussed in more detail below, in many embodiments, transitioning extractor 302 from the first state to the second state may cause a patterned movement in the end effector. In many such embodiments, the pattern of the movement may be optimized to acquire a stent within a target volume. In many embodiments, extractors with pre-curved inner shafts may be utilized in female patients, such as to increase the sweep volume. For example, since the female urethra is relatively short, it can be more common for the urethral portion of the stent to migrate into the bladder. The bladder has a greater volume than the urethra, and, therefore, a greater sweep volume may be more beneficial when attempting to acquire the stent in the bladder as opposed to the urethra. In various embodiments, the sweep motion may be utilized to facilitate decreasing the diameter of the end effector. For example, the sweep motion may allow a 10 French end effector to be utilized while maintaining an acceptable probability of acquiring/capturing a stent for removal. However, in some embodiments without the sweep motion, an 18 French end effector may be needed to maintain an acceptable probability of acquiring/capturing a stent for removal. In various embodiments, an acceptable probability may be between 25 and 100 percent, such as 50 or 75 percent.

Figure 4:
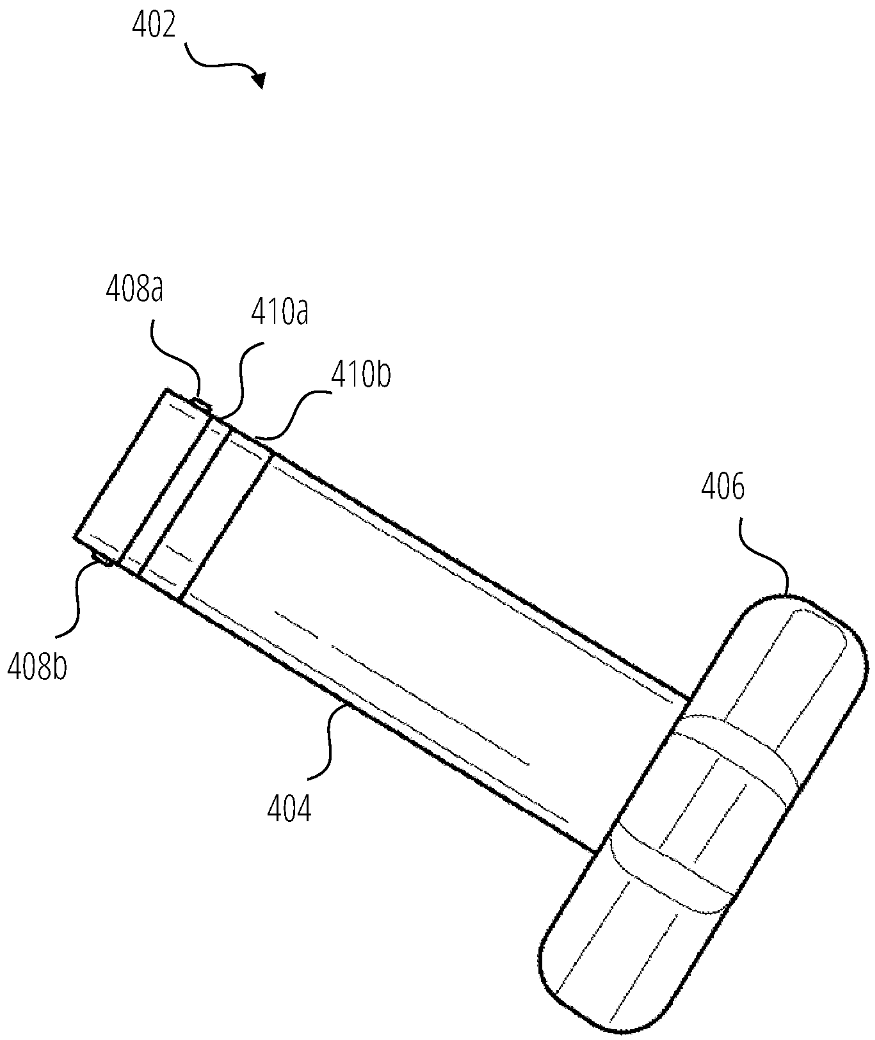
FIG. 4 illustrates an exemplary interface component according to one or more embodiments disclosed hereby.

FIG. 4 illustrates an exemplary interface component 402 according to one or more embodiments disclosed hereby. The interface component 402 may include interface shaft 404, interface 406, pins 408*a*, 408*b*, and indicators 410*a*, 410*b*. In various embodiments, pins 408*a*, 408*b* may be received by slots in a handle body (see e.g., handle body 902 of FIG. 9). In various such embodiments, interaction of the pins 408*a*, 408*b* moving along the slots may cause a variety of movements (e.g., lateral, longitudinal, and/or rotational) in an end effector as the interface 406 is depressed and/or rotated. Accordingly, interaction between pins and slots, or other arrangements (see e.g., FIG. 12), may be utilized to control the degrees of freedom of the end effector and efficiently capture a stent for removal. In many embodiments, movement of the end effector may facilitate capture of a proximal portion of a stent assembly. In one embodiment, pins may be offset lengthwise on the interface shaft 404. In some embodiments, FIG. 4 may include one or more components that are the same or similar to one or more other components of the present disclosure. For example, indicators 410*a*, 410*b* may be the same or similar to indicators 330*a*, 330*b*. Further, one or more components of FIG. 4, or aspects thereof, may be incorporated into other embodiments of the present disclosure, or excluded from the disclosed embodiments, without departing from the scope of this disclosure. For example, interface component 402 may be incorporated into extractor 302 (e.g., by replacing interface 318, interface shaft 320, and indicators 330*a*, 330*b*) without departing from the scope of this disclosure. Further, one or more components of other embodiments of the present disclosure, or aspects thereof, may be incorporated into one or more components of FIG. 4, without departing from the scope of this disclosure. For example, handle body 322 may be incorporated into interface component 402 without departing from the scope of this disclosure. Embodiments are not limited in this context.

Figure 5:
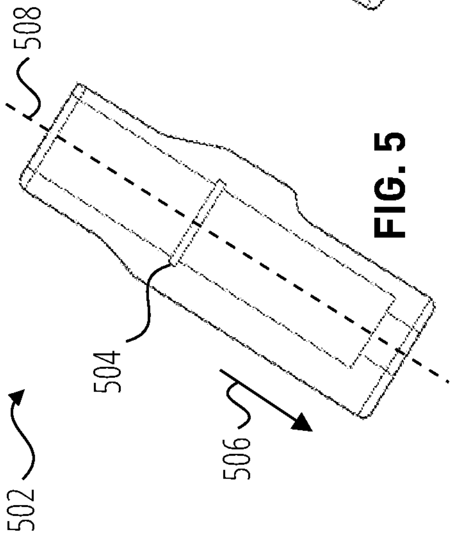
FIG. 5 illustrates an exemplary handle body according to one or more embodiments disclosed hereby.

FIG. 5 illustrates an exemplary handle body 502 according to one or more embodiments disclosed hereby. The handle body 502 may have a longitudinal axis 508, a distal end 506, and include slot 504. It will be appreciated that FIGS. 6-11 illustrate various embodiments of handle bodies with the same orientation as handle body 502. Accordingly, the handle bodies of FIGS. 6-11 may also have a longitudinal axis and a distal end like handle body 502 although they are not labeled. In various embodiments, slot 504 may receive one or more pins of an interface component (e.g., pins 408*a*, 408*b* of interface component 402). In various such embodiments, the slot 504 may guide movement of the pins as the interface 406 is rotated. In some embodiments, FIG. 5 may include one or more components that are the same or similar to one or more other components of the present disclosure. For example, handle body 502 may be the same or similar to handle body 124. Further, one or more components of FIG. 5, or aspects thereof, may be incorporated into other embodiments of the present disclosure, or excluded from the disclosed embodiments, without departing from the scope of this disclosure. For example, slot 504 may be incorporated into handle body 322 without departing from the scope of this disclosure. Further, one or more components of other embodiments of the present disclosure, or aspects thereof, may be incorporated into one or more components of FIG. 5, without departing from the scope of this disclosure. For example, interface component 402 may be incorporated into handle body 502 without departing from the scope of this disclosure. Embodiments are not limited in this context.

In the illustrated embodiment, slot 504 enables rotational movement. In many embodiments, slot 504 may allow rotation of an interface component and an end effector coupled to the interface component. In many such embodiments, the end effector may be moved proximally and distally by displacing the handle body 502 (along with the entire extractor).

Figure 6:
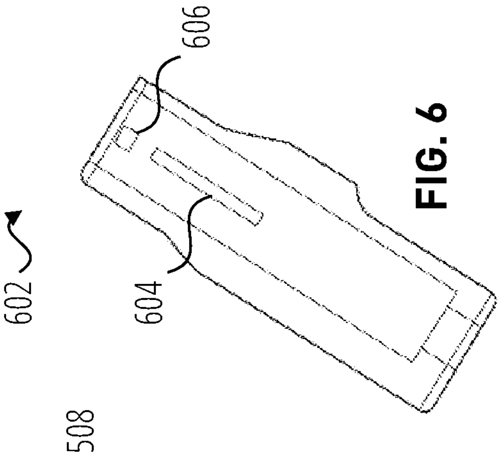
FIG. 6 illustrates an exemplary handle body according to one or more embodiments disclosed hereby.

FIG. 6 illustrates an exemplary handle body 602 according to one or more embodiments disclosed hereby. The handle body 602 may include slot 604 and indicator window 606. In various embodiments, slot 604 may receive a pin of an interface component (e.g., pin 408*a* or pin 408*b* of interface component 402). In various such embodiments, the slot 604 may guide movement of the pin as the interface 406 is depressed. It will be appreciated that handle body 602 may include one or more other longitudinal slots that mirror slot 604 for receipt of additional pins of the interface component (e.g., pin 408*b* or pin 408*a* of interface component 402). In some embodiments, FIG. 6 may include one or more components that are the same or similar to one or more other components of the present disclosure. For example, indicator window 606 may be the same or similar to indicator window 332. Further, one or more components of FIG. 6, or aspects thereof, may be incorporated into other embodiments of the present disclosure, or excluded from the disclosed embodiments, without departing from the scope of this disclosure. For example, indicator window 606 may be incorporated into handle body 502 without departing from the scope of this disclosure. Further, one or more components of other embodiments of the present disclosure, or aspects thereof, may be incorporated into one or more components of FIG. 6, without departing from the scope of this disclosure. For example, interface component 402 may be incorporated into handle body 602 without departing from the scope of this disclosure. Embodiments are not limited in this context.

In the illustrated embodiment, slot 604 enables longitudinal movement. In many embodiments, slot 604 may allow proximal and distal displacement of an interface component and an end effector coupled to the interface component. In many such embodiments, the end effector may be rotated by rotating the handle body 702 (along with the entire extractor).

Figure 7:
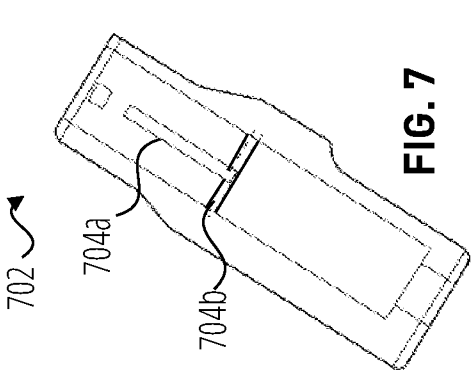
FIG. 7 illustrates an exemplary handle body according to one or more embodiments disclosed hereby.

FIG. 7 illustrates an exemplary handle body 702 according to one or more embodiments disclosed hereby. The handle body 702 may include a longitudinal slot 704*a* connected to a circumferential slot 704*b*. In various embodiments, slots 704*a*, 704*b* may receive one or more pins of an interface component (e.g., pins 408*a*, 408*b* of interface component 402). In various such embodiments, the slots 704*a*, 704*b* may guide movement of the pins as the interface 406 is depressed and/or rotated. It will be appreciated that handle body 702 may include one or more other longitudinal slots that mirror slot 704*a* for receipt of additional pins of the interface component (e.g., pin 408*b* or pin 408*a* of interface component 402). In some embodiments, FIG. 7 may include one or more components that are the same or similar to one or more other components of the present disclosure. For example, handle body 702 may be the same or similar to handle body 124. Further, one or more components of FIG. 7, or aspects thereof, may be incorporated into other embodiments of the present disclosure, or excluded from the disclosed embodiments, without departing from the scope of this disclosure. For example, slots 704*a*, 704*b* may be incorporated into handle body 322 without departing from the scope of this disclosure. Further, one or more components of other embodiments of the present disclosure, or aspects thereof, may be incorporated into one or more components of FIG. 7, without departing from the scope of this disclosure. For example, interface component 402 may be incorporated into handle body 702 without departing from the scope of this disclosure. Embodiments are not limited in this context.

In the illustrated embodiment, slot 704*a* enables longitudinal movement and slot 704*b* enables rotational movement. In many embodiments, slot 704*a* may allow proximal and distal displacement of an interface component and an end effector coupled to the interface component. In many such embodiments, when the interface component is moved distally as far as possible in slot 704*a*, rotation of the interface component, and the end effector coupled thereto, may be facilitated by slot 704*b*. In other words, the pins of the interface component may be moved into the circumferential slot 704*b* when the pins are at the distal end of the longitudinal slot 704*a*. In some embodiments, rotating the interface component and the end effector without having to rotate the handle body 702 (along with the entire extractor) may facilitate keeping track of an amount of rotation.

Figure 8:
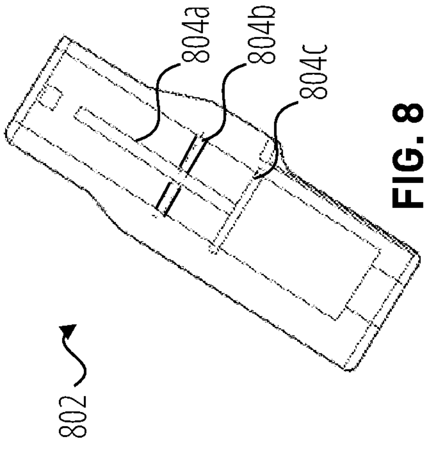
FIG. 8 illustrates an exemplary handle body according to one or more embodiments disclosed hereby.

FIG. 8 illustrates an exemplary handle body 802 according to one or more embodiments disclosed hereby. The handle body 802 may include a longitudinal slot 804*a* connected to a first circumferential slot 804*b*, and a second circumferential slot 804*c*. In various embodiments, slots 804*a*, 804*b*, 804*c* may receive one or more pins of an interface component (e.g., pins 408*a*, 408*b* of interface component 402). In various such embodiments, the slots 804*a*, 804*b*, 804*c* may guide movement of the pins as the interface 406 is depressed and/or rotated. It will be appreciated that handle body 802 may include one or more other longitudinal slots that mirror slot 804*a* for receipt of additional pins of the interface component (e.g., pin 408*b* or pin 408*a* of interface component 402). In some embodiments, FIG. 8 may include one or more components that are the same or similar to one or more other components of the present disclosure. For example, handle body 802 may be the same or similar to handle body 322. Further, one or more components of FIG. 8, or aspects thereof, may be incorporated into other embodiments of the present disclosure, or excluded from the disclosed embodiments, without departing from the scope of this disclosure. For example, slots 804*a*, 804*b*, 804*c* may be incorporated into handle body 124 without departing from the scope of this disclosure. Further, one or more components of other embodiments of the present disclosure, or aspects thereof, may be incorporated into one or more components of FIG. 8, without departing from the scope of this disclosure. For example, interface component 402 may be incorporated into handle body 802 without departing from the scope of this disclosure. Embodiments are not limited in this context.

In the illustrated embodiment, slot 804*a* enables longitudinal movement, slot 804*b* enables rotational movement, and slot 804*c* enables rotational movement. In many embodiments, slot 804*a* may allow proximal and distal displacement of an interface component and an end effector coupled to the interface component. In many such embodiments, when the interface component is moved from the proximal end of slot 804*a* distally to slot 804*b*, rotation of the interface component, and the end effector coupled thereto, may be facilitated by slot 804*b*. Similarly, when the interface component is moved distally as far as possible in slot 804*a*, rotation of the interface component, and the end effector coupled thereto, may be facilitated by slot 804*c*. Accordingly, handle body 802 may facilitate rotational movement at multiple longitudinal displacements. In other embodiments, longitudinally offset pins may rotate via one of slots 804*b*, 804*c*. Some embodiments may include three or more circumferential slots to facilitate rotational movement at multiple longitudinal displacements. In some embodiments, one or more circumferential slots may be replaced with screw slots and/or circumferential slots that extend around the handle body 802 less than 360 degrees.

Figure 9:
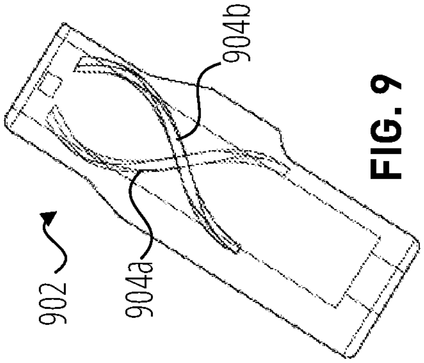
FIG. 9 illustrates an exemplary handle body according to one or more embodiments disclosed hereby.

FIG. 9 illustrates an exemplary handle body 902 according to one or more embodiments disclosed hereby. The handle body 902 may include first and second helical slots 904*a*, 904*b*. In various embodiments, slots 904*a*, 904*b* may each receive a pin of an interface component (e.g., pins 408*a*, 408*b* of interface component 402). In various such embodiments, the slots 904*a*, 904*b* may guide movement of the pins as the interface 406 is depressed. In some embodiments, FIG. 9 may include one or more components that are the same or similar to one or more other components of the present disclosure. For example, handle body 902 may be the same or similar to handle body 322. Further, one or more components of FIG. 9, or aspects thereof, may be incorporated into other embodiments of the present disclosure, or excluded from the disclosed embodiments, without departing from the scope of this disclosure. For example, slots 904*a*, 904*b* may be incorporated into handle body 124 without departing from the scope of this disclosure. Further, one or more components of other embodiments of the present disclosure, or aspects thereof, may be incorporated into one or more components of FIG. 9, without departing from the scope of this disclosure. For example, interface component 402 may be incorporated into handle body 902 without departing from the scope of this disclosure. Embodiments are not limited in this context.

Figure 10:
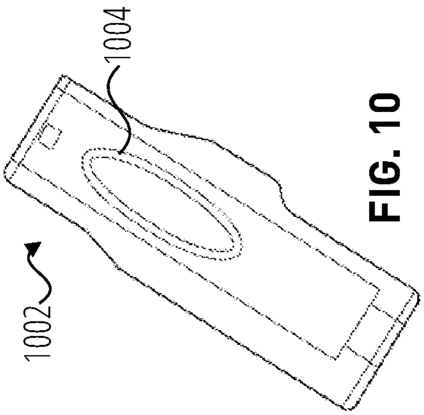
FIG. 10 illustrates an exemplary handle body according to one or more embodiments disclosed hereby.

FIG. 10 illustrates an exemplary handle body 1002 according to one or more embodiments disclosed hereby. The handle body 1002 may include an oval slot 1004. In some embodiments, oval slot 1004 may be replaced with any closed loop shape, such as a rectangle, a circle, a triangle, or a combination thereof. In various embodiments, slot 1004 may receive a pin of an interface component (e.g., pin 408*a* or pin 408*b* of interface component 402). In various such embodiments, the slot 1004 may guide movement of the pin as the interface 406 is depressed. It will be appreciated that handle body 1002 may include one or more other slots that mirror slot 1004 for receipt of additional pins of the interface component (e.g., pin 408*b* or pin 408*a* of interface component 402). In some embodiments, FIG. 10 may include one or more components that are the same or similar to one or more other components of the present disclosure. For example, handle body 1002 may be the same or similar to handle body 124. Further, one or more components of FIG. 10, or aspects thereof, may be incorporated into other embodiments of the present disclosure, or excluded from the disclosed embodiments, without departing from the scope of this disclosure. For example, slot 1004 may be incorporated into handle body 322 without departing from the scope of this disclosure. Further, one or more components of other embodiments of the present disclosure, or aspects thereof, may be incorporated into one or more components of FIG. 10, without departing from the scope of this disclosure. For example, interface component 402 may be incorporated into handle body 1002 without departing from the scope of this disclosure. Embodiments are not limited in this context.

In various embodiments, the slots in handle bodies may cause a desired sweep pattern in the end effector. For example, the handle body 902 may result in a three-dimensional figure eight pattern.

Figure 11:
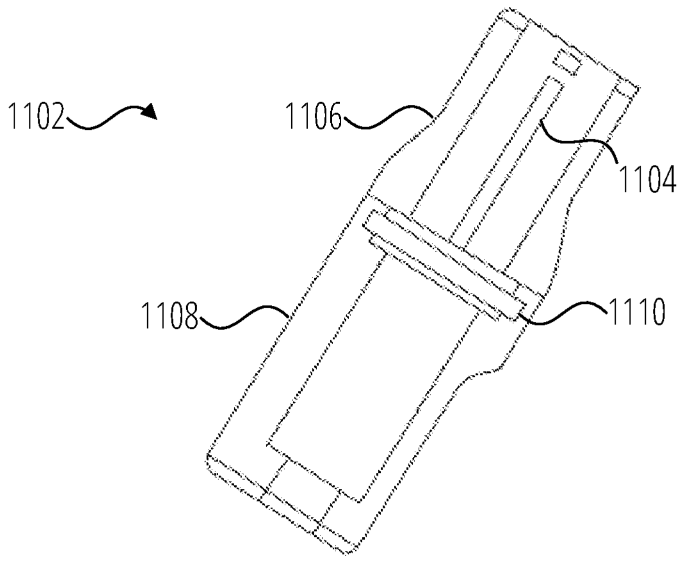
FIG. 11 illustrates an exemplary handle body according to one or more embodiments disclosed hereby.

FIG. 11 illustrates an exemplary handle body 1102 according to one or more embodiments disclosed hereby. The handle body 1102 may include a proximal body portion 1106 with a slot 1104 and a distal body portion 1108 coupled to the proximal body portion 1106 with a revolute joint 1110. In various embodiments, handle body 1102 may enable an end effector to be rotated at any point of extension along slot 1104 without the need to align pins with a circumferential slot. In some embodiments, the revolute joint 1110 includes disk and circular groove joint (or similar) that allows rotational movement without separation. In many embodiments, the handle body 1102 may include one or more tabs (e.g., short perpendicular slots) extending from slot 1104 to lock in the pins of the interface component. In many such embodiments, the tabs may prevent inadvertent retraction, such as when the extractor is biased into a retracted state, such as by biasing member 324. In one or more embodiments, embodiments, the slot 1104 may be replaced with a helical or oval slot. It will be appreciated that handle body 1102 may include one or more other slots that mirror slot 1104 for receipt of additional pins of the interface component (e.g., pin 408*b* or pin 408*a* of interface component 402). In some embodiments, FIG. 11 may include one or more components that are the same or similar to one or more other components of the present disclosure. For example, handle body 1102 may be the same or similar to handle body 322. Further, one or more components of FIG. 11, or aspects thereof, may be incorporated into other embodiments of the present disclosure, or excluded from the disclosed embodiments, without departing from the scope of this disclosure. For example, slot 1104 may be incorporated into handle body 124 without departing from the scope of this disclosure. Further, one or more components of other embodiments of the present disclosure, or aspects thereof, may be incorporated into one or more components of FIG. 11, without departing from the scope of this disclosure. For example, interface component 402 may be incorporated into handle body 1102 without departing from the scope of this disclosure. Embodiments are not limited in this context.

Figure 12:
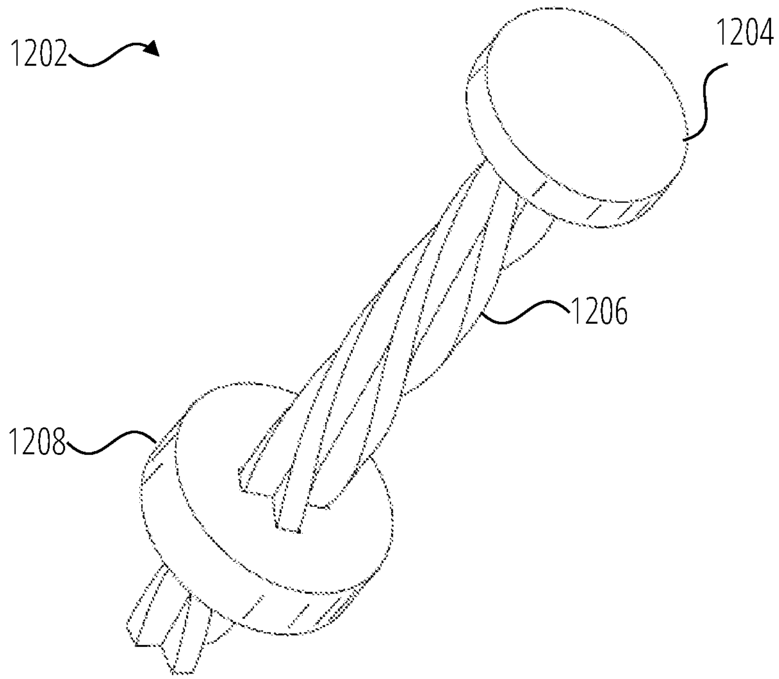
FIG. 12 illustrates an interface component in conjunction with a receiver according to one or more embodiments disclosed hereby.

FIG. 12 illustrates an interface component 1202 in conjunction with a receiver 1208 according to one or more embodiments disclosed hereby. The interface component 1202 may include interface 1204 and interface shaft 1206. In various embodiments, receiver 1208 may form a portion of a handle body. FIG. 12 may illustrate an alternative to pins and slots. As interface 1204 is depressed proximally towards receiver 1208 interaction of the spiral on interface shaft 1206 with the opening in receiver 1208 may cause rotational motion in addition to longitudinal motion. In some embodiments, FIG. 12 may include one or more components that are the same or similar to one or more other components of the present disclosure. For example, interface 1204 may be the same or similar to interface 318. Further, one or more components of FIG. 12, or aspects thereof, may be incorporated into other embodiments of the present disclosure, or excluded from the disclosed embodiments, without departing from the scope of this disclosure. For example, receiver 1208 may be incorporated into handle body 124 and interface shaft 1206 into interface shaft 320 without departing from the scope of this disclosure. Further, one or more components of other embodiments of the present disclosure, or aspects thereof, may be incorporated into one or more components of FIG. 12, without departing from the scope of this disclosure. For example, extractor 302 may be incorporated into interface component 1202 and receiver 1208 without departing from the scope of this disclosure. Embodiments are not limited in this context.

Figures 13A, 13B, 13C:
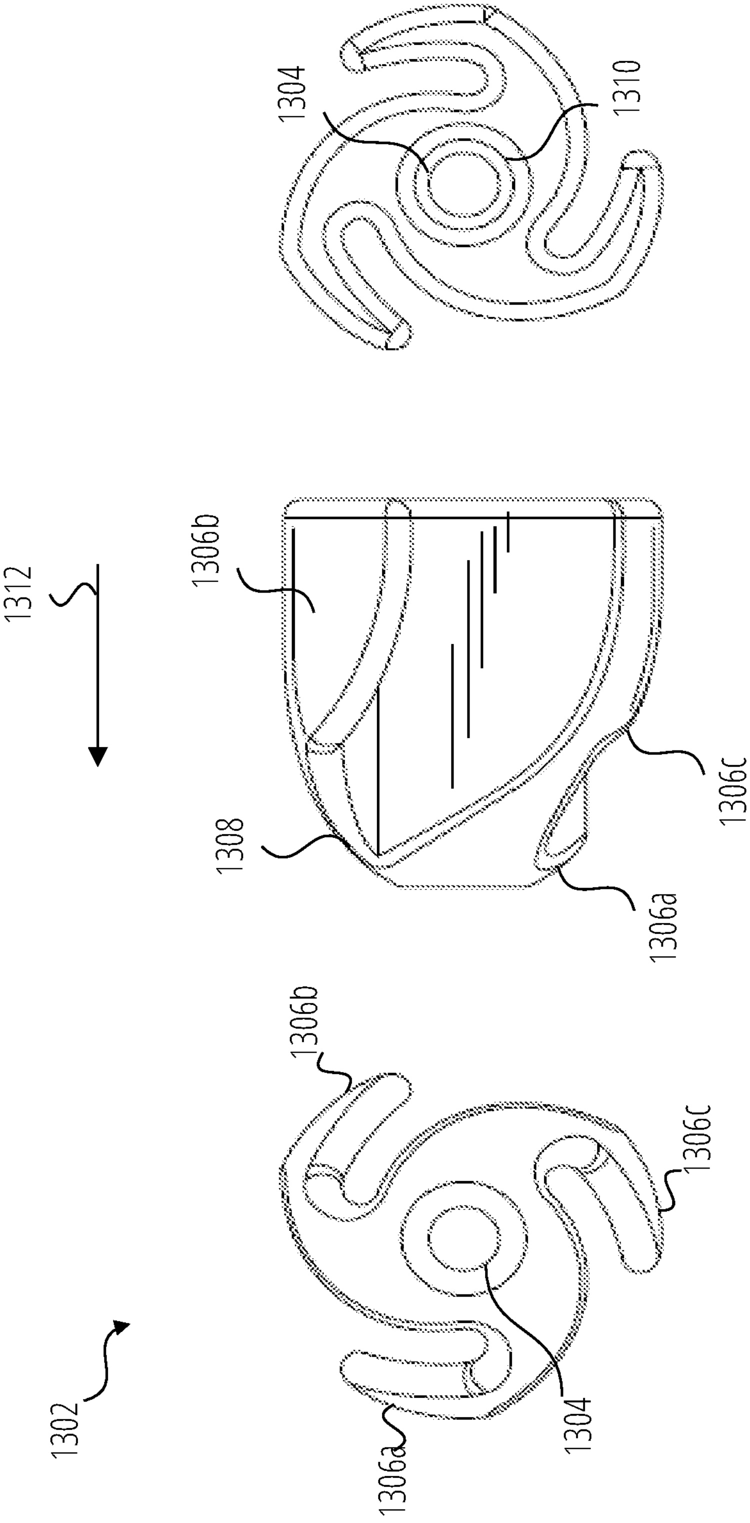
FIGS. 13A-13C illustrates various views of an exemplary end effector according to one or more embodiments disclosed hereby.

FIGS. 13A-13C illustrate various views of an exemplary end effector 1302 according to one or more embodiments disclosed hereby. More specifically, FIG. 13A illustrates a top view, FIG. 13B illustrates a side view, and FIG. 13C illustrates a bottom view. The end effector 1302 may have a distal end 1312 and include a guidewire passage 1304, arms 1306*a*, 1306*b*, 1306*c*, taper 1308, and shaft mount 1310. In various embodiments, the end effector may be extended into a urethra to capture a proximal portion of a stent (or stent assembly) for removal. In many embodiments, the end effector 1302 may couple to a distal end of an extractor (e.g., extractor 102). In many such embodiments, the extractor may be manipulated and/or actuated to induce motion in the end effector configured to facilitate capture and/or retention of a stent (or stent assembly). In some embodiments, FIGS. 13A-13C may include one or more components that are the same or similar to one or more other components of the present disclosure. For example, end effector 1302 may be the same or similar to end effector 308. Further, one or more components of FIGS. 13A-13C, or aspects thereof, may be incorporated into other embodiments of the present disclosure, or excluded from the disclosed embodiments, without departing from the scope of this disclosure. For example, end effector 1302 may include two arms offset by 180 degrees instead of three arms offset by 120 degrees without departing from the scope of this disclosure. Further, one or more components of other embodiments of the present disclosure, or aspects thereof, may be incorporated into one or more components of FIGS. 13A-13C, without departing from the scope of this disclosure. For example, extractor 302 may be utilized in conjunction with end effector 1302 without departing from the scope of this disclosure. In a further example, shaft mount 1310 may be coupled with the inner shaft 310 of extractor 302. Embodiments are not limited in this context.

More generally, end effectors disclosed hereby may have one or more features that facilitate capturing a portion of a stent assembly for removal. For example, end effectors may include one or more of blades, slots, arms, hooks, grooves, and faces to capture a stent. In some embodiments, end effectors may include one or more of round, oval, elliptical, hexagonal, or polygonal profiles. In various embodiments, end effectors may include right-handed, left-handed, or neutral features.

Figure 14C:
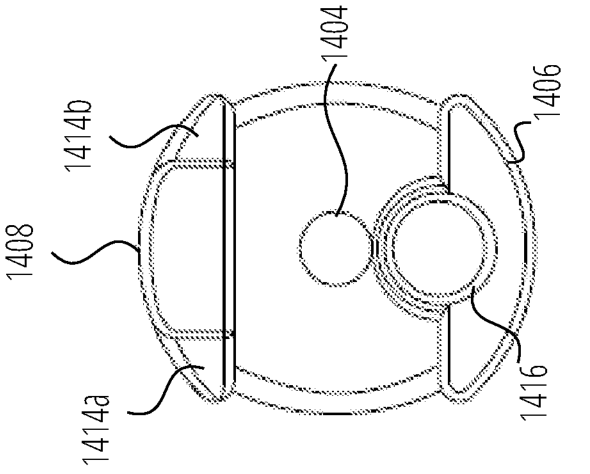
FIGS. 14A-14C illustrates various views of an exemplary end effector according to one or more embodiments disclosed hereby.
Figure 14B:
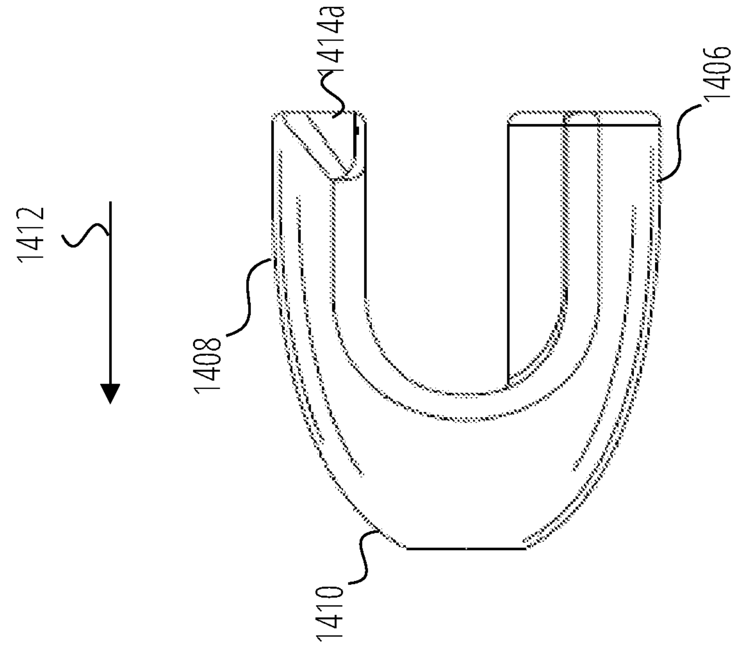
Figure 14A:
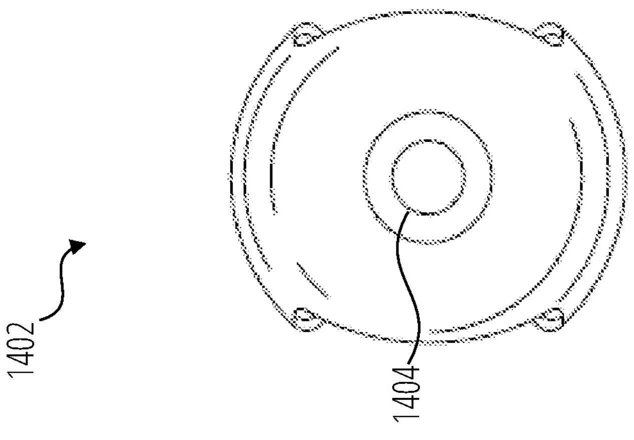

FIGS. 14A-14C illustrate various views of an exemplary end effector 1402 according to one or more embodiments disclosed hereby. More specifically, FIG. 14A illustrates a top view, FIG. 14B illustrates a side view, and FIG. 14C illustrates a bottom view. The end effector 1402 may have a distal end 1412 and include a guidewire passage 1404, base 1406, hook 1408, taper 1410, hook features 1414*a*, 1414*b*, and shaft mount 1416. In various embodiments, the end effector may be extended into a urethra to capture a proximal portion of a stent (or stent assembly) for removal. In many embodiments, the end effector 1402 may couple to a distal end of an extractor (e.g., extractor 102). In many such embodiments, the extractor may be manipulated and/or actuated to induce motion in the end effector configured to facilitate capture of a stent (or stent assembly). In some embodiments, FIGS. 14A-14C may include one or more components that are the same or similar to one or more other components of the present disclosure. For example, end effector 1402 may be the same or similar to end effector 108. Further, one or more components of FIGS. 14A-14C, or aspects thereof, may be incorporated into other embodiments of the present disclosure, or excluded from the disclosed embodiments, without departing from the scope of this disclosure. For example, hook features 1414*a*, 1414*b* may be incorporated into arms 1306*a*, 1306*b*, 1306*c* without departing from the scope of this disclosure. Further, one or more components of other embodiments of the present disclosure, or aspects thereof, may be incorporated into one or more components of FIGS. 14A-14C, without departing from the scope of this disclosure. For example, extractor 302 may be utilized in conjunction with end effector 1402 without departing from the scope of this disclosure. In a further example, shaft mount 1416 may be coupled with the inner shaft 110 of extractor 102. Embodiments are not limited in this context.

Figure 15C:
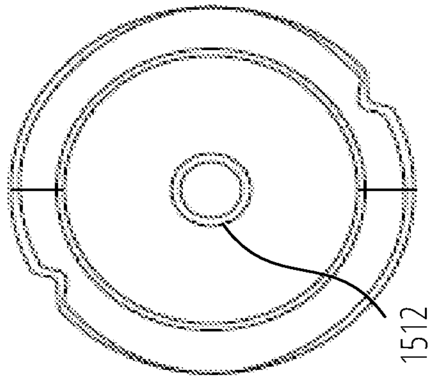
FIGS. 15A-15C illustrates various views of an exemplary end effector according to one or more embodiments disclosed hereby.
Figure 15B:
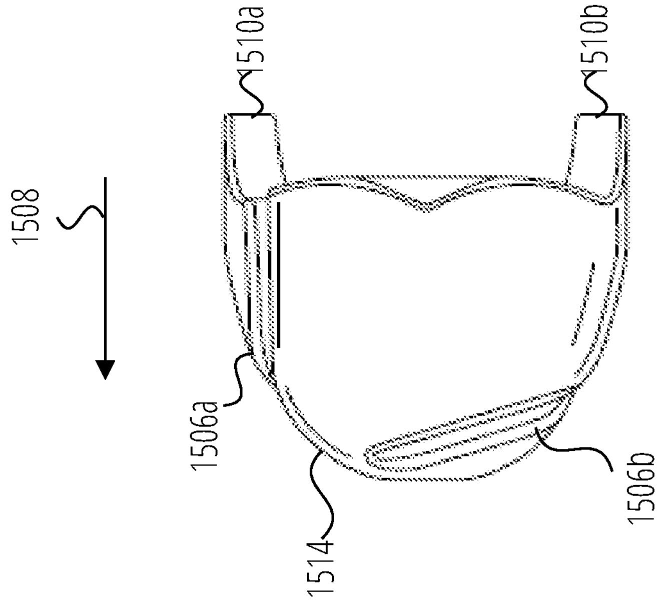
Figure 15A:
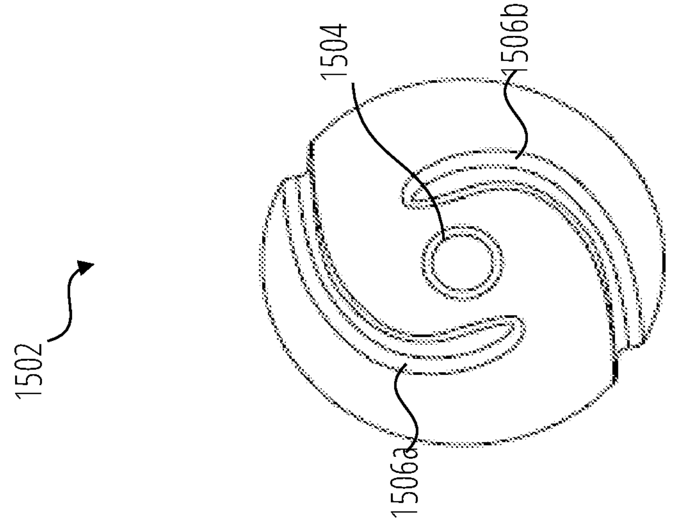

FIGS. 15A-15C illustrate various views of an exemplary end effector 1502 according to one or more embodiments disclosed hereby. More specifically, FIG. 15A illustrates a top view, FIG. 15B illustrates a side view, and FIG. 15C illustrates a bottom view. The end effector 1502 may have a distal end 1508 and include a guidewire passage 1504, slots 1506*a*, 1506*b*, wings 1510*a*, 1510*b*, taper 1514, and shaft mount 1512. In various embodiments, the end effector may be extended into a urethra to capture a proximal portion of a stent (or stent assembly) for removal. In many embodiments, the end effector 1502 may couple to a distal end of an extractor (e.g., extractor 102). In many such embodiments, the extractor may be manipulated and/or actuated to induce motion in the end effector configured to facilitate capture of a stent (or stent assembly). In various embodiments, slots 1506*a*, 1506*b* may include helical indentations that assist in pulling the extractor into the body, or maintaining a position of the extractor, as the extractor is actuated to capture a stent. In some embodiments, FIGS. 15A-15C may include one or more components that are the same or similar to one or more other components of the present disclosure. For example, end effector 1502 may be the same or similar to end effector 308. Further, one or more components of FIGS. 15A-15C, or aspects thereof, may be incorporated into other embodiments of the present disclosure, or excluded from the disclosed embodiments, without departing from the scope of this disclosure. For example, end effector 1502 may include three slots offset by 120 degrees instead of two slots offset by 180 degrees without departing from the scope of this disclosure. Further, one or more components of other embodiments of the present disclosure, or aspects thereof, may be incorporated into one or more components of FIGS. 15A-15C, without departing from the scope of this disclosure. For example, extractor 302 may be utilized in conjunction with end effector 1502 without departing from the scope of this disclosure. In a further example, shaft mount 1512 may be coupled with the inner shaft 310 of extractor 302. Embodiments are not limited in this context.

Figure 16C:
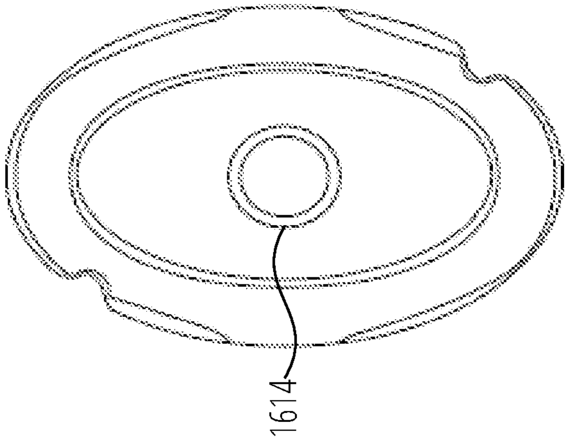
FIGS. 16A-16C illustrates various views of an exemplary end effector according to one or more embodiments disclosed hereby.
Figure 16B:
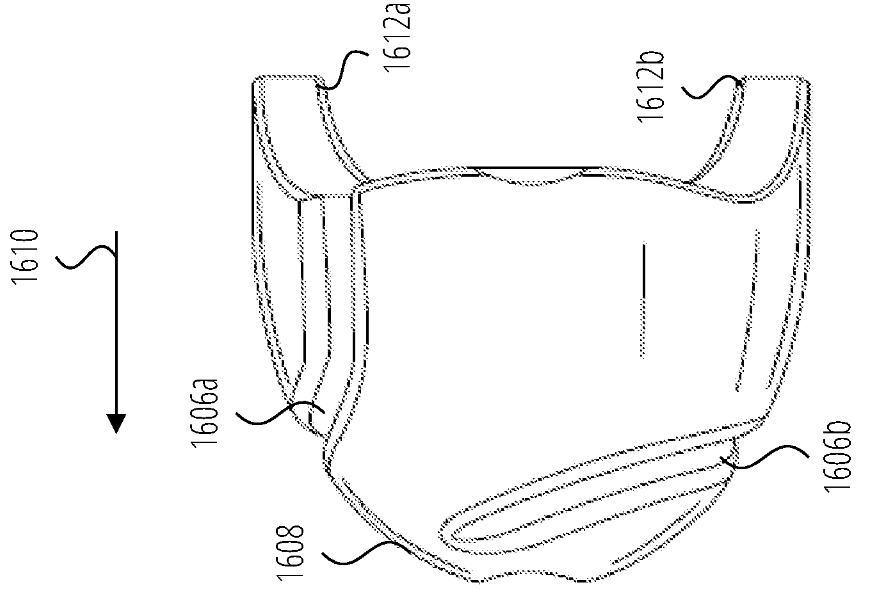
Figure 16A:
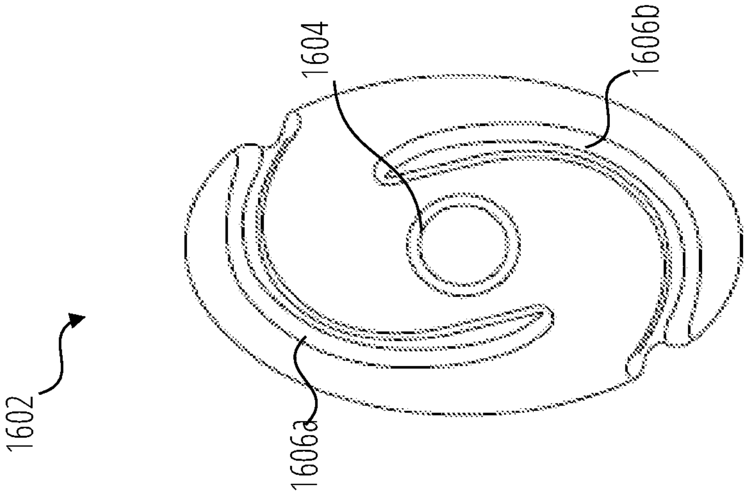

FIGS. 16A-16C illustrate various views of an exemplary end effector 1402 according to one or more embodiments disclosed hereby. More specifically, FIG. 16A illustrates a top view, FIG. 16B illustrates a side view, and FIG. 16C illustrates a bottom view. The end effector 1602 may have a distal end 1610 and include a guidewire passage 1604, slots 1606*a*, 1606*b*, taper 1608, wings 1612*a*, 1612*b*, and shaft mount 1614. In various embodiments, the end effector may be extended into a urethra to capture a proximal portion of a stent (or stent assembly) for removal. In many embodiments, the end effector 1602 may couple to a distal end of an extractor (e.g., extractor 302). In many such embodiments, the extractor may be manipulated and/or actuated to induce motion in the end effector configured to facilitate capture of a stent (or stent assembly). In various embodiments, slots 1606*a*, 1606*b* may include helical indentations that assist in pulling the extractor into the body, or maintaining a position of the extractor, as the extractor is actuated to capture a stent. In some embodiments, FIGS. 16A-16C may include one or more components that are the same or similar to one or more other components of the present disclosure. For example, end effector 1602 may be the same or similar to end effector 108. Further, one or more components of FIGS. 16A-16C, or aspects thereof, may be incorporated into other embodiments of the present disclosure, or excluded from the disclosed embodiments, without departing from the scope of this disclosure. For example, wings 1510*a*, 1510*b* may be incorporated into arms 1306*a*, 1306*b*, 1306*c* without departing from the scope of this disclosure. Further, one or more components of other embodiments of the present disclosure, or aspects thereof, may be incorporated into one or more components of FIGS. 16A-16C, without departing from the scope of this disclosure. For example, extractor 302 may be utilized in conjunction with end effector 1602 without departing from the scope of this disclosure. In a further example, shaft mount 1614 may be coupled with the inner shaft 110 of extractor 102. Embodiments are not limited in this context.

Figure 17:
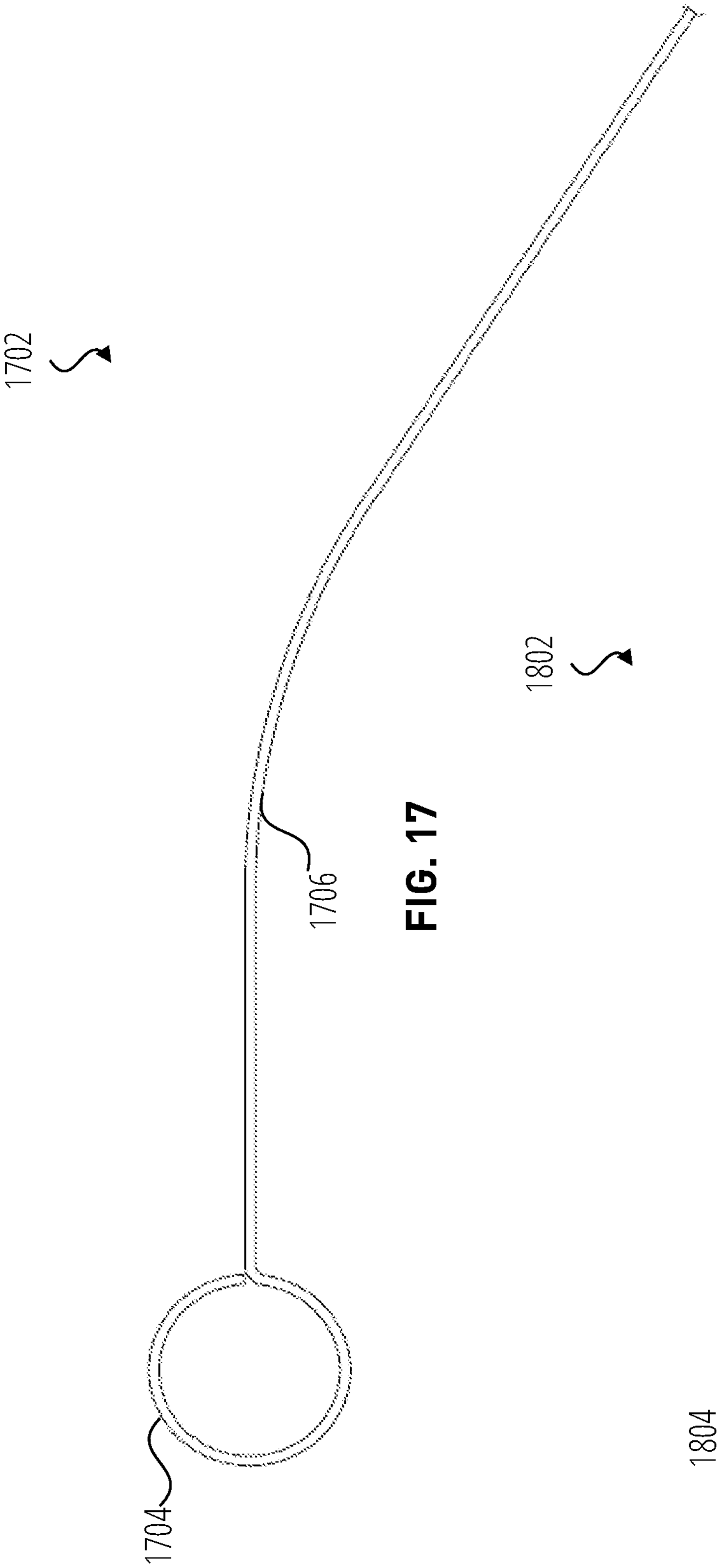
FIG. 17 illustrates an exemplary effector component according to one or more embodiments disclosed hereby.

FIG. 17 illustrates an exemplary effector component 1702 according to one or more embodiments disclosed hereby. The effector component 1702 may include end effector 1704 and curved inner shaft 1706. More generally, an effector component may refer to an end effector and at least a portion of a shaft extending from the end effector. In various embodiments, effector component 1702 may be formed from an elongate member, such as a wire. In various such embodiments, the elongate member may be bent into the illustrated form. In some embodiments, wires may be coated, such as with a polymer or a hydrophilic coating. In one embodiment, effector component 1702 may be a polymer, such as a molded polymer. In some embodiments, the end effector may be extended into a urethra to capture a proximal portion of a stent (or stent assembly) for removal. In many embodiments, the end effector 1704 may couple to a distal end of an extractor (e.g., extractor 102). In many such embodiments, the extractor may be manipulated and/or actuated to induce motion in the end effector configured to facilitate capture of a stent (or stent assembly). In some embodiments, FIG. 17 may include one or more components that are the same or similar to one or more other components of the present disclosure. For example, curved inner shaft 1706 may be the same or similar to inner shaft 110. Further, one or more components of FIG. 17, or aspects thereof, may be incorporated into other embodiments of the present disclosure, or excluded from the disclosed embodiments, without departing from the scope of this disclosure. For example, effector component 1702 may be incorporated into extractor 302 without departing from the scope of this disclosure. Further, one or more components of other embodiments of the present disclosure, or aspects thereof, may be incorporated into one or more components of FIG. 17, without departing from the scope of this disclosure. For example, interface component 402 may be coupled to a proximal end of curved inner shaft 1706 without departing from the scope of this disclosure. Embodiments are not limited in this context.

Figure 18:
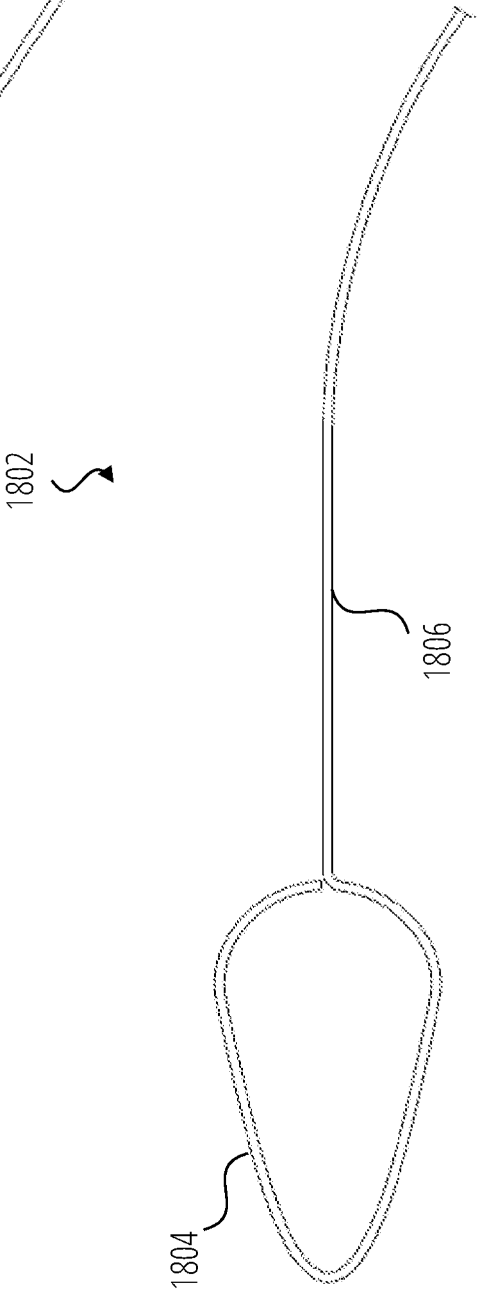
FIG. 18 illustrates an exemplary effector component according to one or more embodiments disclosed hereby.

FIG. 18 illustrates an exemplary effector component 1802 according to one or more embodiments disclosed hereby. The effector component 1802 may include end effector 1804 and curved inner shaft 1806. In various embodiments, effector component 1802 may be formed from an elongate member, such as a wire. In various such embodiments, the elongate member may be bent into the illustrated form. In some embodiments, the end effector may be extended into a urethra to capture a proximal portion of a stent (or stent assembly) for removal. In many embodiments, the end effector 1804 may couple to a distal end of an extractor (e.g., extractor 302). In many such embodiments, the extractor may be manipulated and/or actuated to induce motion in the end effector configured to facilitate capture of a stent (or stent assembly). In some embodiments, FIG. 18 may include one or more components that are the same or similar to one or more other components of the present disclosure. For example, curved inner shaft 1806 may be the same or similar to inner shaft 310. Further, one or more components of FIG. 18, or aspects thereof, may be incorporated into other embodiments of the present disclosure, or excluded from the disclosed embodiments, without departing from the scope of this disclosure. For example, effector component 1702 may be incorporated into extractor 102 without departing from the scope of this disclosure. Further, one or more components of other embodiments of the present disclosure, or aspects thereof, may be incorporated into one or more components of FIG. 18, without departing from the scope of this disclosure. For example, interface shaft 122 may be coupled to a proximal end of curved inner shaft 1806 without departing from the scope of this disclosure. Embodiments are not limited in this context.

Figure 19:
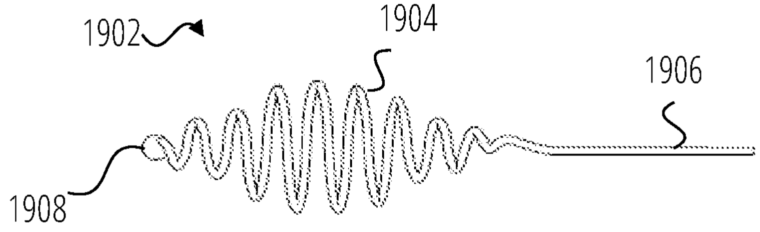
FIG. 19 illustrates an exemplary effector component according to one or more embodiments disclosed hereby.

FIG. 19 illustrates an exemplary effector component 1902 according to one or more embodiments disclosed hereby. The effector component 1902 may include end effector 1904, inner shaft 1906, and ball tip 1908. In various embodiments, effector component 1902 may be formed from an elongate member, such as a wire. In various such embodiments, the elongate member may be bent into the illustrated form. In several embodiments, ball tip 1908 may comprise a ball weld. In some embodiments, the end effector may be extended into a urethra to capture a proximal portion of a stent (or stent assembly) for removal. In many embodiments, the end effector 1904 may couple to a distal end of an extractor (e.g., extractor 302). In many such embodiments, the extractor may be manipulated and/or actuated to induce motion in the end effector configured to facilitate capture of a stent (or stent assembly). In some embodiments, FIG. 19 may include one or more components that are the same or similar to one or more other components of the present disclosure. For example, inner shaft 1906 may be the same or similar to inner shaft 110. Further, one or more components of FIG. 19, or aspects thereof, may be incorporated into other embodiments of the present disclosure, or excluded from the disclosed embodiments, without departing from the scope of this disclosure. For example, effector component 1902 may be incorporated into extractor 302 without departing from the scope of this disclosure. Further, one or more components of other embodiments of the present disclosure, or aspects thereof, may be incorporated into one or more components of FIG. 19, without departing from the scope of this disclosure. For example, interface shaft 320 may be coupled to a proximal end of inner shaft 1906 without departing from the scope of this disclosure. Embodiments are not limited in this context.

Figure 20:
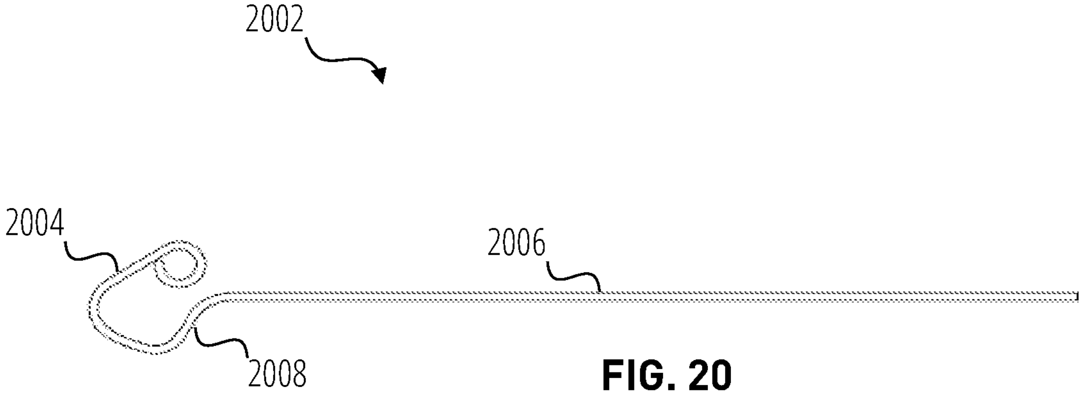
FIG. 20 illustrates an exemplary effector component according to one or more embodiments disclosed hereby.

FIG. 20 illustrates an exemplary effector component 2002 according to one or more embodiments disclosed hereby. The effector component 2002 may include end effector 2004, inner shaft 2006, and shaft offset 2008. In various embodiments, effector component 2002 may be formed from an elongate member, such as a wire. In various such embodiments, the elongate member may be bent into the illustrated form. In some embodiments, the end effector may be extended into a urethra to capture a proximal portion of a stent (or stent assembly) for removal. In many embodiments, the end effector 2004 may couple to a distal end of an extractor (e.g., extractor 302). In many such embodiments, the extractor may be manipulated and/or actuated to induce motion in the end effector configured to facilitate capture of a stent (or stent assembly). In some embodiments, FIG. 20 may include one or more components that are the same or similar to one or more other components of the present disclosure. For example, inner shaft 2006 may be the same or similar to inner shaft 310. Further, one or more components of FIG. 20, or aspects thereof, may be incorporated into other embodiments of the present disclosure, or excluded from the disclosed embodiments, without departing from the scope of this disclosure. For example, effector component 2002 may be incorporated into extractor 102 without departing from the scope of this disclosure. Further, one or more components of other embodiments of the present disclosure, or aspects thereof, may be incorporated into one or more components of FIG. 20, without departing from the scope of this disclosure. For example, interface component 402 may be coupled to a proximal end of inner shaft 2006 without departing from the scope of this disclosure. Embodiments are not limited in this context.

Figure 21A:
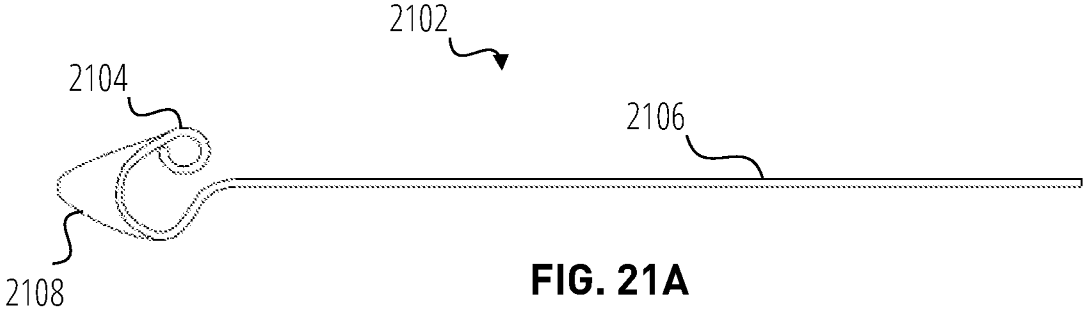
FIG. 21A illustrates a side view of an effector component according to one or more embodiments disclosed hereby.
Figure 21B:
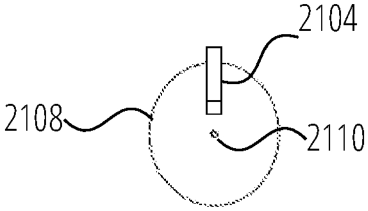
FIG. 21B illustrates a front view of an effector component according to one or more embodiments disclosed hereby.

FIGS. 21A and 21B illustrate various views of an exemplary effector component 2102 according to one or more embodiments disclosed hereby. More specifically, FIG. 21A illustrates a side view and FIG. 21B illustrates front view. The effector component 2102 may include end effector 2104, inner shaft 2106, shield 2108, and guidewire passage 2110. In various embodiments, effector component 2102, except for the shield 2108, may be formed from an elongate member, such as a wire. In various such embodiments, the elongate member may be bent into the illustrated form. In many embodiments, the shield 2108 may comprise a cone or dome shape that is tapered. In several embodiments, shield 2108 may comprise a polymer, such as a molded polymer component. In some embodiments, the end effector may be extended into a urethra to capture a proximal portion of a stent (or stent assembly) for removal. In many embodiments, the end effector 2104 may couple to a distal end of an extractor (e.g., extractor 302). In many such embodiments, the extractor may be manipulated and/or actuated to induce motion in the end effector configured to facilitate capture of a stent (or stent assembly). In some embodiments, FIGS. 21A and 21B may include one or more components that are the same or similar to one or more other components of the present disclosure. For example, inner shaft 2106 may be the same or similar to inner shaft 110. Further, one or more components of FIGS. 21A and 21B, or aspects thereof, may be incorporated into other embodiments of the present disclosure, or excluded from the disclosed embodiments, without departing from the scope of this disclosure. For example, effector component 2102 may be incorporated into extractor 302 without departing from the scope of this disclosure. Further, one or more components of other embodiments of the present disclosure, or aspects thereof, may be incorporated into one or more components of FIGS. 21A and 21B, without departing from the scope of this disclosure. For example, interface shaft 404 may be coupled to a proximal end of inner shaft 2106 without departing from the scope of this disclosure. Embodiments are not limited in this context.

Figure 22A:
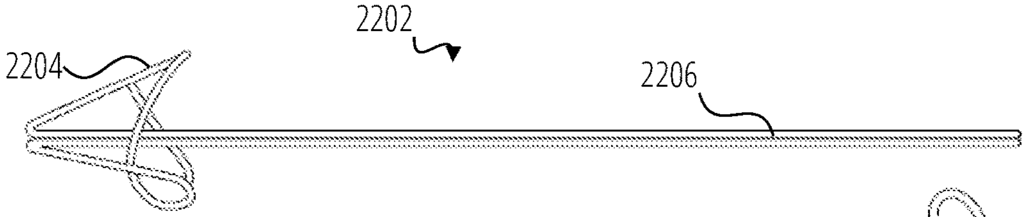
FIG. 22A illustrates a side view of an effector component according to one or more embodiments disclosed hereby.
Figure 22B:
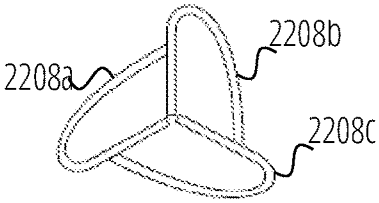
FIG. 22B illustrates a front view of an effector component according to one or more embodiments disclosed hereby.

FIGS. 22A and 22B illustrate various views of an exemplary effector component 2202 according to one or more embodiments disclosed hereby. More specifically, FIG. 22A illustrates a side view and FIG. 22B illustrates front view. The effector component 2202 may include end effector 2204, inner shaft 2206, and elongate members 2208*a*, 2208*b*, 2208*c*. In various embodiments, the elongate members 2208*a*, 2208*b*, 2208*c* may comprise three wires. In many embodiments, the elongate members may be coupled together, such as via welding, adhesives, knots, crimps, or molding. In several embodiments, the elongate members may be bent into the illustrated form. In some embodiments, the end effector may be extended into a urethra to capture a proximal portion of a stent (or stent assembly) for removal. In many embodiments, the end effector 2204 may couple to a distal end of an extractor (e.g., extractor 102). In many such embodiments, the extractor may be manipulated and/or actuated to induce motion in the end effector configured to facilitate capture of a stent (or stent assembly). In some embodiments, FIGS. 22A and 22B may include one or more components that are the same or similar to one or more other components of the present disclosure. For example, inner shaft 2206 may be the same or similar to inner shaft 310. Further, one or more components of FIGS. 22A and 22B, or aspects thereof, may be incorporated into other embodiments of the present disclosure, or excluded from the disclosed embodiments, without departing from the scope of this disclosure. For example, effector component 2202 may be incorporated into extractor 102 without departing from the scope of this disclosure. Further, one or more components of other embodiments of the present disclosure, or aspects thereof, may be incorporated into one or more components of FIGS. 22A and 22B, without departing from the scope of this disclosure. For example, interface shaft 320 may be coupled to a proximal end of inner shaft 2206 without departing from the scope of this disclosure. Embodiments are not limited in this context.

Figure 23:
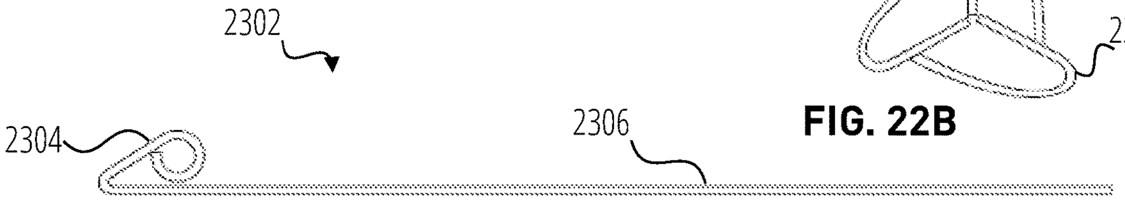
FIG. 23 illustrates an exemplary effector component according to one or more embodiments disclosed hereby.

FIG. 23 illustrates an exemplary effector component 2302 according to one or more embodiments disclosed hereby. The effector component 2302 may include end effector 2304 and inner shaft 2306. In various embodiments, effector component 2302 may be formed from an elongate member, such as a wire. In various such embodiments, the elongate member may be bent into the illustrated form. In some embodiments, the end effector may be extended into a urethra to capture a proximal portion of a stent (or stent assembly) for removal. In many embodiments, the end effector 2304 may couple to a distal end of an extractor (e.g., extractor 302). In many such embodiments, the extractor may be manipulated and/or actuated to induce motion in the end effector configured to facilitate capture of a stent (or stent assembly). In several embodiments, contact between end effector 2304 and inner shaft 2306 may be utilized to retain a captured portion of a suture assembly. In some embodiments, FIG. 23 may include one or more components that are the same or similar to one or more other components of the present disclosure. For example, inner shaft 2306 may be the same or similar to inner shaft 310. Further, one or more components of FIG. 23, or aspects thereof, may be incorporated into other embodiments of the present disclosure, or excluded from the disclosed embodiments, without departing from the scope of this disclosure. For example, effector component 2302 may be incorporated into extractor 102 without departing from the scope of this disclosure. Further, one or more components of other embodiments of the present disclosure, or aspects thereof, may be incorporated into one or more components of FIG. 23, without departing from the scope of this disclosure. For example, interface component 402 may be coupled to a proximal end of inner shaft 2306 without departing from the scope of this disclosure. Embodiments are not limited in this context.

Figure 24:
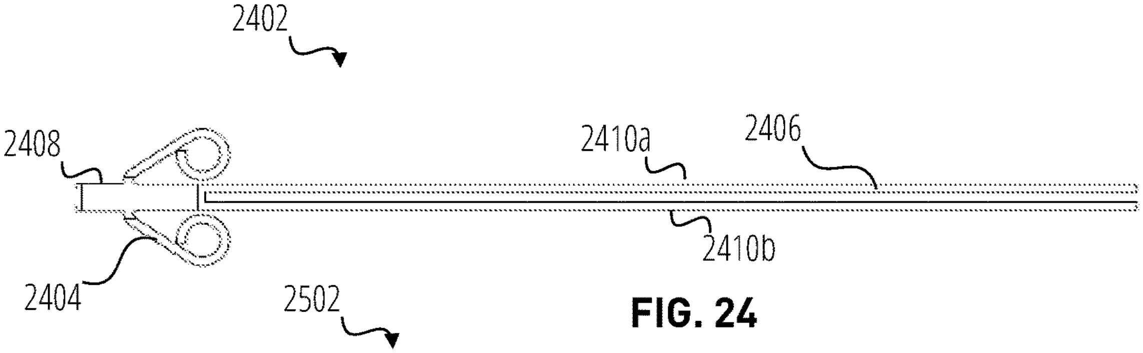
FIG. 24 illustrates an exemplary effector component according to one or more embodiments disclosed hereby.

FIG. 24 illustrates various views of an exemplary effector component 2402 according to one or more embodiments disclosed hereby. The effector component 2402 may include end effector 2404, inner shaft 2406, insert 2408, and elongate members 2410*a*, 2410*b*. In various embodiments, the elongate members 2410*a*, 2410*b* may comprise two wires. In many embodiments, the elongate members may be coupled together, such as via welding or an adhesive. In various such embodiments, the elongate member may be bent into the illustrated form. In one embodiment, the insert 2408 may be molded, such as from a polymer. In various embodiments, the insert 2408 may include a guidewire passage. In some embodiments, the end effector may be extended into a urethra to capture a proximal portion of a stent (or stent assembly) for removal. In many embodiments, the end effector 2204 may couple to a distal end of an extractor (e.g., extractor 302). In many such embodiments, the extractor may be manipulated and/or actuated to induce motion in the end effector configured to facilitate capture of a stent (or stent assembly). In some embodiments, FIG. 24 may include one or more components that are the same or similar to one or more other components of the present disclosure. For example, elongate member 2410*a* may be the same or similar to effector component 2302. Further, one or more components of FIG. 24, or aspects thereof, may be incorporated into other embodiments of the present disclosure, or excluded from the disclosed embodiments, without departing from the scope of this disclosure. For example, effector component 2402 may be incorporated into extractor 302 without departing from the scope of this disclosure. Further, one or more components of other embodiments of the present disclosure, or aspects thereof, may be incorporated into one or more components of FIG. 24, without departing from the scope of this disclosure. For example, interface shaft 122 may be coupled to a proximal end of inner shaft 2406 without departing from the scope of this disclosure. Embodiments are not limited in this context.

Figure 25:
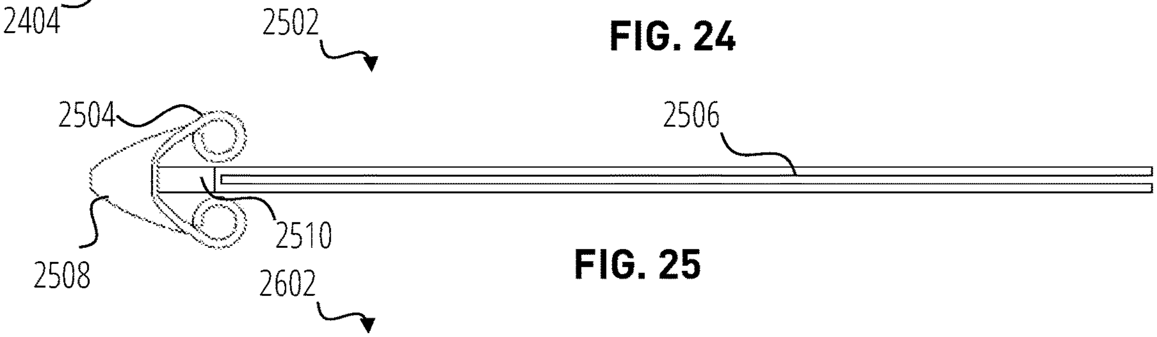
FIG. 25 illustrates an exemplary effector component according to one or more embodiments disclosed hereby.

FIG. 25 illustrates an exemplary effector component 2502 according to one or more embodiments disclosed hereby. The effector component 2502 may include end effector 2504, inner shaft 2506, shield 2508, and insert 2510. In various embodiments, effector component 2502, except for the shield 2508, may be formed from an elongate member, such as a wire. In various such embodiments, the elongate member may be bent into the illustrated form. In some embodiments, the end effector may be extended into a urethra to capture a proximal portion of a stent (or stent assembly) for removal. In many embodiments, the end effector 2504 may couple to a distal end of an extractor (e.g., extractor 302). In many such embodiments, the extractor may be manipulated and/or actuated to induce motion in the end effector configured to facilitate capture of a stent (or stent assembly). In some embodiments, FIG. 25 may include one or more components that are the same or similar to one or more other components of the present disclosure. For example, effector component 2502 may be the same or similar to effector component 2402 except for shield 2508. Further, one or more components of FIG. 25, or aspects thereof, may be incorporated into other embodiments of the present disclosure, or excluded from the disclosed embodiments, without departing from the scope of this disclosure. For example, effector component 2502 may be incorporated into extractor 102 without departing from the scope of this disclosure. Further, one or more components of other embodiments of the present disclosure, or aspects thereof, may be incorporated into one or more components of FIG. 25, without departing from the scope of this disclosure. For example, interface component 402 may be coupled to a proximal end of inner shaft 2506 without departing from the scope of this disclosure. Embodiments are not limited in this context.

Figure 26:
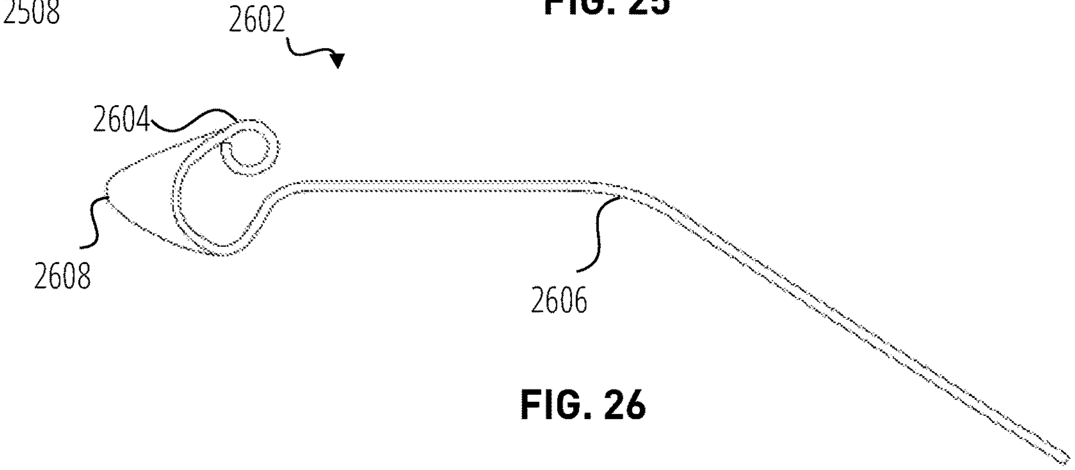
FIG. 26 illustrates an exemplary effector component according to one or more embodiments disclosed hereby.

FIG. 26 illustrates an exemplary effector component 2602 according to one or more embodiments disclosed hereby. The effector component 2602 may include end effector 2604, curved inner shaft 2606, and shield 2608. In various embodiments, effector component 2602, except for the shield 2608, may be formed from an elongate member, such as a wire. In various such embodiments, the elongate member may be bent into the illustrated form. In some embodiments, the end effector may be extended into a urethra to capture a proximal portion of a stent (or stent assembly) for removal. In many embodiments, the end effector 2604 may couple to a distal end of an extractor (e.g., extractor 302). In many such embodiments, the extractor may be manipulated and/or actuated to induce motion in the end effector configured to facilitate capture of a stent (or stent assembly). In various embodiments, the curved inner shaft 2606 may result in a sweeping motion when the effector component 2602 is rotated, such as due to actuation (see e.g., FIGS. 7-10). In some embodiments, FIG. 26 may include one or more components that are the same or similar to one or more other components of the present disclosure. For example, effector component 2602 may be the same or similar to effector component 2102 except for curved inner shaft 2606. Further, one or more components of FIG. 26, or aspects thereof, may be incorporated into other embodiments of the present disclosure, or excluded from the disclosed embodiments, without departing from the scope of this disclosure. For example, effector component 2602 may be incorporated into extractor 302 without departing from the scope of this disclosure. Further, one or more components of other embodiments of the present disclosure, or aspects thereof, may be incorporated into one or more components of FIG. 26, without departing from the scope of this disclosure. For example, interface shaft 320 may be coupled to a proximal end of curved inner shaft 2606 without departing from the scope of this disclosure. Embodiments are not limited in this context.

Figure 27A:
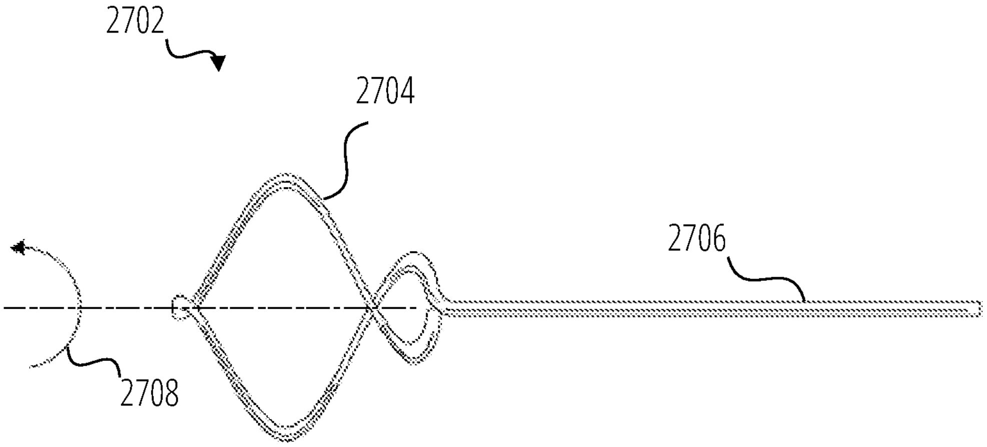
FIG. 27A illustrates a side view of an effector component according to one or more embodiments disclosed hereby.
Figure 27B:
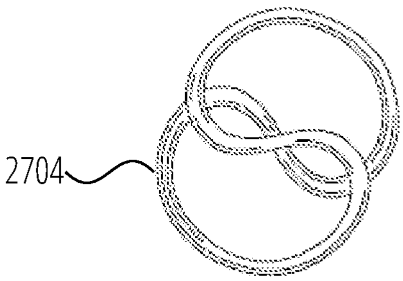
FIG. 27B illustrates a front view of an effector component according to one or more embodiments disclosed hereby.

FIGS. 27A and 27B illustrate various views of an exemplary effector component 2702 according to one or more embodiments disclosed hereby. More specifically, FIG. 27A illustrates a side view and FIG. 27B illustrates front view. The effector component 2702 may include end effector 2704 and inner shaft 2706. In various embodiments, effector component 2702 may be formed from an elongate member, such as a wire. In various such embodiments, the elongate member may be bent into the illustrated form. In some embodiments, the end effector may be extended into a urethra to capture a proximal portion of a stent (or stent assembly) for removal. In many embodiments, the end effector 2704 may couple to a distal end of an extractor (e.g., extractor 102). In many such embodiments, the extractor may be manipulated and/or actuated to induce motion in the end effector configured to facilitate capture of a stent (or stent assembly). In some embodiments, FIGS. 27A and 27B may include one or more components that are the same or similar to one or more other components of the present disclosure. For example, inner shaft 2706 may be the same or similar to inner shaft 110. Further, one or more components of FIGS. 27A and 27B, or aspects thereof, may be incorporated into other embodiments of the present disclosure, or excluded from the disclosed embodiments, without departing from the scope of this disclosure. For example, effector component 2702 may be incorporated into extractor 102 without departing from the scope of this disclosure. Further, one or more components of other embodiments of the present disclosure, or aspects thereof, may be incorporated into one or more components of FIGS. 27A and 27B, without departing from the scope of this disclosure. For example, interface shaft 320 may be coupled to a proximal end of inner shaft 2706 without departing from the scope of this disclosure. Embodiments are not limited in this context.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases “at least one”, “one or more”, and “and/or”, as used herein, are open-ended expressions that are both conjunctive and disjunctive in operation. The terms “a”, “an”, “the”, “first”, “second”, etc., do not preclude a plurality. For example, the term “a” or “an” entity, as used herein, refers to one or more of that entity. As such, the terms “a” (or “an”), “one or more” and “at least one” can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader’s understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term “comprises/comprising” does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

All of the devices and/or methods disclosed and claimed hereby can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method disclosed hereby without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:

an interface coupled to a proximal portion of an interface shaft, wherein a distal portion of the interface shaft comprises a pin;

an end effector coupled to a distal portion of an inner shaft, the end effector is configured to engage a deployed stent for extraction; and a handle body coupled to the distal portion of the interface shaft and a proximal portion of the inner shaft, wherein the handle body includes a slot configured to receive the pin of the interface shaft and guide motion of the interface and the end effector with respect to the handle body, and wherein the end effector, the inner shaft, and the interface shaft define a lumen configured for passage of a guidewire.

2. The medical device of claim 1, wherein the slot is configured to interact with the pin to restrict motion of the interface and the end effector in at least one direction with respect to the handle body.

3. The medical device of claim 1, wherein displacement of the interface along a longitudinal axis causes displacement of the end effector along the longitudinal axis.

4. The medical device of claim 1, wherein the slot is configured to interact with the pin to cause the end effector to rotate about a longitudinal axis in response to displacement of the interface along the longitudinal axis.

5. The medical device of claim 1, wherein the slot comprises a helical shape or an oval shape.

6. The medical device of claim 1, wherein the slot extends about an inner circumference of the handle body at a first location to form a first circle.

7. The medical device of claim 6, wherein the slot extends about an inner circumference of the handle body at a second location to form a second circle, and the slot connects the first and second circles.

8. The medical device of claim 1, wherein the inner shaft is flexible and pre-curved.

9. The medical device of claim 1, comprising an outer shaft with a proximal end coupled to the handle body and a distal end coupled to an effector shield, wherein the inner shaft is disposed within the outer shaft.

10. The medical device of claim 9, wherein the effector shield has an outer diameter greater than an outer diameter of the end effector.

11. The medical device of claim 1, wherein the end effector comprises one or more grooves configured to engage the deployed stent for extraction.

12. The medical device of claim 1, the handle body including an indicator window and the interface shaft including a first indicator and a second indicator, wherein the first indicator is visible via the indicator window when the end effector is in a first position relative to the handle body and the second indicator is visible via the indicator window when the end effector is in a second position relative to the handle body.

13. The medical device of claim 1, wherein the inner shaft is coupled to the handle body via a biasing member.

14. The medical device of claim 1, comprising an adjustable stop, wherein the adjustable stop comprises a diameter greater than the diameter of the end effector.

15. A method comprising:

inserting a proximal end of an extractor into a urethra of a body, the extractor comprising:

an interface coupled to a proximal portion of an interface shaft, an end effector coupled to a distal portion of an inner shaft, and a handle body coupled to a distal portion of the interface shaft and a proximal portion of the inner shaft;

transitioning the extractor from a retracted state to an extended state to capture a stent fully deployed in the urethra; and removing the proximal end of the extractor from the urethra to remove the stent from the body, wherein the distal portion of the interface shaft comprises a pin, and wherein the handle body includes a slot configured to receive the pin of the interface shaft and guide motion of the interface and the end effector with respect to the handle body when the extractor is transitioned from the retracted state to the extended state, and wherein the slot comprises a helical shape or an oval shape to at least partially rotate the end effector when the extractor is transitioned from the retracted state to the extended state.

16. The method of claim 15, comprising depressing the interface to transition the extractor from the retracted state to the extended state.

17. A system comprising:

an extractor comprising:

an interface coupled to a proximal portion of an interface shaft, wherein a distal portion of the interface shaft comprises a pin, an end effector coupled to a distal portion of an inner shaft, and a handle body coupled to the distal portion of the interface shaft and a proximal portion of the inner shaft, wherein the handle body includes a slot configured to receive the pin of the interface shaft and guide motion of the interface and the end effector with respect to the handle body; and a ureteral stent configured to be deployed in a urethra, the ureteral stent including a loop configured for capture by the end effector of the extractor.

18. The system of claim 17, wherein displacement of the interface along a longitudinal axis causes displacement of the end effector along the longitudinal axis.

19. The system of claim 17, wherein the slot is configured to interact with the pin to cause the end effector to rotate about a longitudinal axis in response to displacement of the interface along the longitudinal axis.

20. The system of claim 17, wherein the inner shaft is flexible and pre-curved.

* * * * *